United States Patent [19]

Baker et al.

[11] Patent Number: 5,260,293
[45] Date of Patent: Nov. 9, 1993

[54] PYRAZINES, PYRIMIDINES AND PYRIDAZINES USEFUL IN THE TREATMENT OF SENILE DEMENTIA

[75] Inventors: Raymond Baker, Much Hadham; Leslie J. Street, Harlow; John Saunders, Ware, all of England

[73] Assignee: Merck Sharp & Dohme Limited, Hoddesdon, England

[21] Appl. No.: 775,630

[22] Filed: Oct. 10, 1991

[63] Continuation-in-part of 299,906, Jan. 23, 1989, abandoned.

[30] Foreign Application Priority Data

Jan. 30, 1988 [GB] United Kingdom ............... 8802101
Jun. 27, 1988 [GB] United Kingdom ............... 8815225
Jul. 26, 1988 [GB] United Kingdom ............... 8817812
Sep. 8, 1988 [GB] United Kingdom ............... 8821088

[51] Int. Cl.⁵ .................. A61K 31/55; A61K 31/495; A61K 31/50; C07D 413/04; C07D 453/02; C07D 451/02; C07D 209/52
[52] U.S. Cl. ........................ 514/214; 514/210; 514/216; 514/252; 514/253; 514/254; 514/256; 514/269; 514/272; 514/274; 540/582; 540/598; 540/601; 544/238; 544/298; 544/300; 544/310; 544/315; 544/316; 544/317; 544/318; 544/319; 544/320; 544/322; 544/324; 544/328; 544/331; 544/333; 544/405
[58] Field of Search ............ 544/298, 315, 331, 333, 544/405, 238, 300, 310, 315–320, 322, 324, 328, 405; 514/269, 272, 274, 210, 214, 216, 252–254, 256; 540/582, 598, 601

[56] References Cited

FOREIGN PATENT DOCUMENTS

0122580 9/1987 European Pat. Off. .

OTHER PUBLICATIONS

Chem. Abstracts vol. 81, No. 15 (Oct. 14, 1974) Columbus, Ohio p. 469.
Journal of Med. Chem. vol. 24, No. 12, (1981) pp. 1475–1482.
Bull. Des Societes Chimiques Belges, vol. 75, No. 1-2, (1966) pp. 5–16.
Vestnik Slovenskega Kemijskega Drustva, vol. 33, No. 3, pp. 197–215.
TIPS, Feb. 1988, pp. 44–48.
TIPS, Feb. 1986, pp. 56–59.
Nature 283, (5742), pp. 90–92 (Jan. 3, 1980).

*Primary Examiner*—Cecilia Tsang
*Attorney, Agent, or Firm*—Robert J. North; William H. Nicholson; Joseph F. DiPrima

[57] ABSTRACT

The present invention provides pyrazines, pyridazines or pyrimidines, or salts or prodrugs thereof, substituted on one of the ring carbon atoms thereof with a non-aromatic azacyclic or azabicyclic ring system; and independently substituted on each of the other ring carbon atoms with a substituent of low lipophilicity or a hydrocarbon substituent; which compounds stimulate central muscarinic acetylcholine receptors and therefore are useful in the treatment of neurological and mental illnesses.

9 Claims, No Drawings

PYRAZINES, PYRIMIDINES AND PYRIDAZINES USEFUL IN THE TREATMENT OF SENILE DEMENTIA

The present invention relates to a class of substituted pyrazine, pyridazine and pyrimidine compounds which stimulate central muscarinic acetylcholine receptors and therefore are useful in the treatment of neurological and mental illnesses whose clinical manifestations are due to cholinergic deficiency. Such diseases include presenile and senile dementia (also known as Alzheimer's disease and senile dementia of the Alzheimer type respectively), Huntington's chorea, tardive dyskinesia, hyperkinesia, mania and Tourette Syndrome. Alzheimer's disease, the most common dementing illness, is a slowly progressive neurological disorder characterised by marked deficits in cognitive functions including memory, attention, language and visual perception capabilities.

Published European Patent Application No. 239309 discloses a class of oxadiazole compounds having a substituent of low lipophilicity, which are useful in the treatment of neurodegenerative disorders. It has now been found that a class of pyrazines, pyridazines and pyrimidines having a broader range of substituents also stimulate cholinergic transmission. There is no disclosure of pyrazine, pyridazine or pyrimidine structures in EP-A-0239309.

It is believed that the enhancement of cholinergic transmission demonstrated by the compounds of this invention is achieved either directly by stimulating postsynaptic receptors, or indirectly by potentiating acetylcholine release.

The compounds of the present invention are pyrazines, pyridazines or pyrimidines, or salts or prodrugs thereof, substituted on one of the ring carbon atoms thereof with a non-aromatic azacyclic or azabicyclic ring system; and independently substituted on each of the other ring carbon atoms with a substituent of low lipophilicity or a hydrocarbon substituent.

Accordingly the present invention provides a compound of formula I:

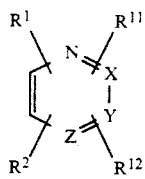

or a salt or prodrug thereof; wherein
one of X, Y and Z represents nitrogen and the remainder represent carbon atoms;
$R^1$ represents a non-aromatic azacyclic or azabicyclic ring system; and
$R^2$, $R^{11}$ and $R^{12}$ independently represent hydrogen, halogen, $-CF_3$, $-OR^6$, $-NR^6R^7$, $-NHOR^6$, $-NHNH_2$, $-CN$, $COR^8$, or a substituted or unsubstituted, saturated or unsaturated hydrocarbon group; wherein $R^6$ is hydrogen, $C_{1-6}$ alkyl, $C_{2-6}$ alkenyl or $C_{2-6}$ alkynyl, $R^7$ is hydrogen, $C_{1-6}$ alkyl or $-COCH_3$, and $R^8$ represents $-OR^6$ or $-NR^6R^7$.

The novel compounds of this invention may be represented by structural formulae IA, IB or IC:

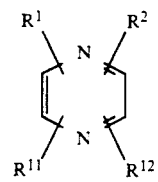

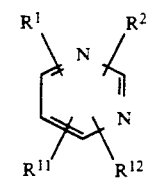

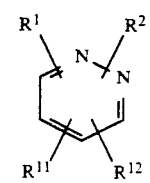

or salts or prodrugs thereof; wherein $R^1$, $R^2$, $R^{11}$ and $R^{12}$ are as defined above.

Preferably the ring is a pyrazine of formula IA, i.e. having the nitrogen atoms at the 1,4 positions.

The azacyclic or azabicyclic ring system is a non-aromatic ring system containing one nitrogen atom as the sole heteroatom. Suitably the ring system contains from 4 to 10 ring atoms, preferably from 5 to 8 ring atoms. Preferably, the ring system contains a tertiary amino nitrogen atom in a caged structure. The bicyclic systems may be fused, spiro or bridged. Preferably, the nitrogen atom is at a bridgehead in a bicyclic system. Examples of suitable ring systems for the group $R^1$ include the following:

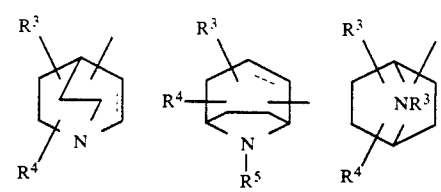

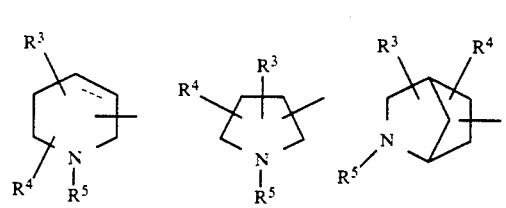

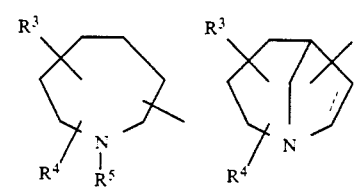

-continued

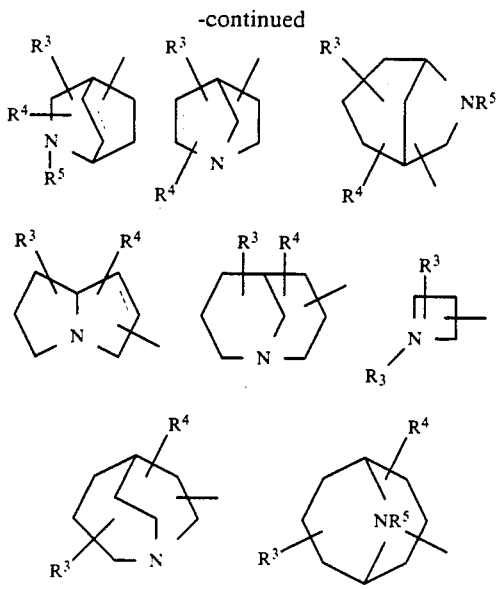

wherein the broken line represents an optional chemical bond;

the substituents $R^3$ and $R^4$ may be present at any position, including the point of attachment to the ring of structure I, and independently represent hydrogen, $C_{1-4}$ alkyl, halogen, $C_{1-4}$ alkoxy, hydroxy, carboxy or $C_{1-4}$ alkoxycarbonyl; or $R^3$ and $R^4$ together represent carbonyl; and $R^5$ represents hydrogen or $C_{1-4}$ alkyl.

It will be appreciated that the nitrogen atom in the azacyclic or azabicyclic ring will carry a lone pair of electrons.

Suitably the group $R^3$ is hydrogen or methyl; and $R^4$ is hydrogen, $C_{1-4}$ alkoxy, $C_{1-4}$ alkyl, $C_{1-4}$ alkoxycarbonyl, halogen or hydroxy, preferably methoxy, methyl, fluoro, chloro, hydroxy or methoxycarbonyl. Preferably one or both of $R^3$ and $R^4$ is hydrogen.

Preferably the group $R^5$ represents hydrogen or methyl.

Suitably the azacyclic or azabicyclic ring system is pyrrolidine, piperidine, tetrahydropyridine, azanorbornane, quinuclidine, isoquinuclidine, azabicyclo[2.2.2]octene or 1-azabicyclo[3.2.1]octane, any of which may in particular be either unsubstituted or substituted with methyl, hydroxy, fluoro, chloro or methoxycarbonyl.

The term "substituent of low lipophilicity" is intended to indicate that the group has a Rekker f value (hydrophobic fragment constant; see R. F. Rekker, "The Hydrophobic Fragmental Constant", Elsevier, 1977) of not greater than 1.5. For example, the methyl group has a value of 0.7 and the ethyl group a value of 1.26.

Thus, where the compounds in accordance with the present invention are substituted by a substituent of low lipophilicity, this substituent may be, for example, hydrogen, halogen, $-CF_3$, $-OR^{17}$, $-N(R^{17})_2$, $-N-HOR^{17}$, $-NHNH_2$, $-CN$, $-COR^{18}$, $C_{2-5}$ alkenyl, $C_{2-5}$ alkynyl, $C_{1-2}$ alkyl, or $C_{1-2}$ alkyl substituted with $-OR^{17}$, $-N(R^{17})_2$, $-SR^{17}$, $-CO_2R^{17}$, $-CON(R^{17})_2$ or halogen; wherein $R^{17}$ is hydrogen or $C_{1-2}$ alkyl and $R^{18}$ represents $-OR^{17}$ or $-NHR^{17}$.

When the groups $R^2$, $R^{11}$ and/or $R^{12}$ in formula IA, IB or IC are hydrocarbon substituents, they may be $C_{1-15}$ alkyl, $C_{2-15}$ alkenyl, $C_{2-15}$ alkynyl, aryl or aralkyl. The alkyl, alkenyl or alkynyl groups may be straight, branched or cyclic groups. Suitably the alkyl group comprises from 1 to 6 carbon atoms. The hydrocarbon group(s) may carry one or more substituents. Suitable substituent groups include halogen, $-OR^6$, $-CF_3$, $-NR^6R^7$, $-NO_2$, optionally substituted aryl, keto, $-SR^6$, $-SOR^6$, $-SO_2R^6$, $-CO_2R^6$ and $-CONR^6R^7$; wherein $R^6$ and $R^7$ are as defined with respect to formula I above.

Substituents most suitable for the aryl group include chloro, bromo, methoxy, $C_{1-6}$ alkyl, methoxycarbonyl, trifluoromethyl, nitro and $-NR^6R^7$.

Preferably the groups $R^2$, $R^{11}$ and $R^{12}$ independently represent hydrogen, halogen, $-CF_3$, $-OR^6$, $-NHR^6$, $-NHNH_2$, $-CN$, $-COR^8$, phenyl($C_{1-3}$)alkyl, $C_{3-6}$ cycloalkyl, adamantyl, $C_{2-6}$ alkenyl, $C_{2-6}$ alkynyl, $C_{1-6}$ alkyl, or $C_{1-6}$ alkyl substituted with $-OR^6$, $-NHR^6$, $-SR^6$, $-CO_2R^6$, $-CON(R^6)_2$ or halogen. Particular values of the groups $R^2$, $R^{11}$ and/or $R^{12}$ are hydrogen, hydroxy, chloro, methyl, ethyl, isopropyl, cyclopropyl, benzyl, adamantyl, amino, dimethylamino, methoxy, ethoxy, isopropoxy, n-butoxy, allyloxy, propargyloxy, methoxycarbonyl and ethoxycarbonyl. A preferred value is dimethylamino.

One group of prodrugs of compounds of this invention have a substituent on the pyrazine, pyridazine or pyrimidine ring which is hydrolysable in vivo to an amino group.

Groups which are hydrolysable in vivo to an amino group on the compounds of this invention may be readily ascertained by administering the compound to a human or animal and detecting, by conventional analytical techniques, the presence of the corresponding compound having an amino substituent in the urine of a human or animal. Examples of such groups include, for example, amido and urethane substituents, in particular a group of formula $-NH.Q$, wherein Q represents CHO, COR or $CO_2R$, and R represents an optionally substituted hydrocarbon group.

In this context, the hydrocarbon group R includes groups having up to 20 carbon atoms, suitably up to 10 carbon atoms, conveniently up to 6 carbon atoms. Suitable groups R include $C_{1-9}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, and aryl($C_{1-6}$)alkyl. The alkyl group R may be straight or branched chain and may contain, for example, up to 12 carbon atoms, suitably from 1 to 6 carbon atoms. In particular the group may be substituted methyl, ethyl, n- or iso-propyl, n-, sec-, iso- or tert-butyl, n- or iso-heptyl, or n- or iso-octyl. Suitable cycloalkyl groups include cyclopentyl and cyclohexyl. The aryl group R includes phenyl and naphthyl optionally substituted with up to five, preferably up to three, substituent groups.

One sub-class of compounds within the scope of the present invention is represented by formula IIA, IIB or IIC:

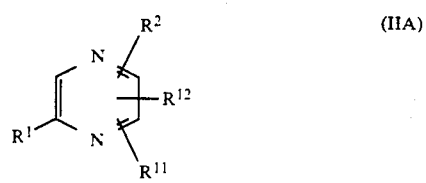

(IIA)

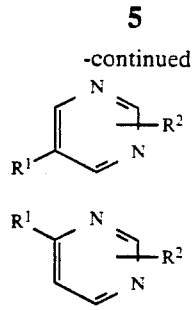

wherein $R^1$, $R^2$, $R^{11}$ and $R^{12}$ are as defined above; in particular wherein $R^1$ represents pyrrolidine, quinuclidine, tetrahydropyridine, piperidine, dehydrotropane, pyrrolizidine, azanorbornane, isoquinuclidine or azabicyclo[2.2.2]octene, any of which groups $R^1$ may be optionally substituted with $C_{1-3}$ alkyl, hydroxy, halogen or $C_{1-3}$ alkoxycarbonyl; and $R^2$, $R^{11}$ and $R^{12}$ independently represent hydrogen, halogen, $-OR^6$, $C_{1-6}$ alkyl, phenyl($C_{1-3}$)alkyl, $C_{3-6}$ cycloalkyl, amino or dimethylamino. Preferably $R^1$ represents 1-azanorbornane or quinuclidine.

Specific compounds within the scope of the present invention include the following, and salts and prodrugs thereof:

3-(2-pyrazinyl)-1-azabicyclo[2.2.2]octan-3-ol;
3-(2-pyrazinyl)-1-azabicyclo[2.2.2]octane;
3-[2-(6-methylpyrazin)yl]-1-azabicyclo[2.2.2]octan-3-ol;
3-[2-(6-methylpyrazin)yl]-1-azabicyclo[2.2.2]octane;
3-[2-(6-methoxypyrazin)yl]-1-azabicyclo[2.2.2]octane;
3-[2-(6-hydroxypyrazin)yl]-1-azabicyclo[2.2.2]-octane;
3-(2-pyrazinyl)-1-azabicyclo[2.2.1]heptan-3-ol;
3-(2-pyrazinyl)-1-azabicyclo[2.2.1]heptane;
6-(2-pyrazinyl)-1-azabicyclo[3.2.1]octan-6-ol;
6-(2-pyrazinyl)-1-azabicyclo[3.2.1]octane;
3-(5-pyrimidinyl)-1-azabicyclo[2.2.2]octan-3-ol;
3-(5-pyrimidinyl)-1-azabicyclo[2.2.2]octane;
3-[5-(2-methylpyrimidin)yl]-1-azabicyclo[2.2.2]octane;
3-(2-pyrazinyl)-1-azabicyclo[2.2.1]heptan-5-ol;
3-fluoro-3-(2-pyrazinyl)-1-azabicyclo[2.2.1]heptane;
1-methyl-3-(2-pyrazinyl)pyrrolidine;
3-[2-(6-methoxypyrazin)yl]-1-azabicyclo[2.2.1]heptane;
3-[2-(3-methylpyrazin)yl]-1-azabicyclo[2.2.2]octan-3-ol;
3-[2-(3-methylpyrazin)yl]-3-chloro-1-azabicyclo[2.2.2]octane;
3-[2-(3-methylpyrazin)yl]-1-azabicyclo[2.2.2]oct-2-ene;
3-[2-(3-methylpyrazin)yl]-1-azabicyclo[2.2.2]octane;
3-[2-(6-methylpyrazin)yl]-1-azabicyclo 3-[2-(6-methylpyrazin)yl]-1-azabicyclo[2.2.1]heptan-3-ol;
3-[2-(6-methylpyrazin)yl]-3-chloro-1-azabicyclo[2.2.1]heptane;
3-[2-(6-methylpyrazin)yl]-1-azabicyclo[2.2.1]heptane;
3-[2-(6-dimethylaminopyrazin)yl]-1-azabicyclo[2.2.1]heptan-3-ol;
3-[2-(6-dimethylaminopyrazin)yl]-1-azabicyclo[2.2.1]heptane;
3-[2-(6-ethoxypyrazin)yl]-1-azabicyclo[2.2.1]heptan-3-ol;
3-[2-(6-ethoxypyrazin)yl]-1-azabicyclo[2.2.1]heptane;
6-[2-(6-methoxypyrazin)yl]-1-azabicyclo[3.2.1]octane;
3-[2-(3,6-dimethylpyrazin)yl]-1-azabicyclo[2.2.1]heptan-3-ol;
3-[2-(3,6-dimethylpyrazin)yl]-1-azabicyclo[2.2.1]heptane;
3-[2-(3,5-dimethylpyrazin)yl]-1-azabicyclo[2.2.1]heptane;
3-[5-(2,3-dimethylpyrazin)yl]-1-azabicyclo[2.2.1]heptane;
3-[2-(3-ethylpyrazin)yl]-1-azabicyclo[2.2.2]octane;
3-[2-(3-ethylpyrazin)yl]-1-azabicyclo[2.2.1]heptane;
3-[2-(6-isopropoxypyrazin)yl]-1-azabicyclo[2.2.1]heptane;
3-[2-(6-propargyloxypyrazin)yl]-1-azabicyclo[2.2.1]heptane;
3-[2-(6-chloropyrazin)yl]-3-methoxycarbonyl-1-azabicyclo[2.2.2]octane;
3-[2-(6-chloropyrazin)yl]-1-azabicyclo[2.2.2]octane;
3-[2-(5-methylpyrazin)yl]-1-azabicyclo[2.2.2]octane;
3-[2-(6-allyloxypyrazin)yl]-1-azabicyclo[2.2.2]octane;
3-[2-(3-methylpyrazin)yl]-1,2,5,6-tetrahydropyridine;
3-[2-(6-methylpyrazin)yl]-1,2,5,6-tetrahydropyridine;
6-[2-(3-methylpyrazin)yl]-2-azabicyclo[2.2.2]octane;
3-[2-(6-allyloxypyrazin)yl]-1-azabicyclo[2.2.1]heptane;
3-[2-(3-methylpyrazin)yl]-1-azabicyclo[2.2.1]heptane;
3-[2-(6-chloropyrazin)yl]-1-azabicyclo[2.2.1]heptane;
6-[2-(6-chloropyrazin)yl]-2-azabicyclo[2.2.2]octane;
6-[2-(6-methoxypyrazin)yl]-2-azabicyclo[2.2.2]octane;
3-[2-(6-n-butoxypyrazin)yl]-1-azabicyclo[2.2.2]octane;
3-[2-(3,5,6-trimethylpyrazin)yl]-1-azabicyclo[2.2.1]heptane;
6-(2-pyrazinyl)-2-azabicyclo[2.2.2]octane; and
3-[4-(2-chloropyrimidin)yl]-1-azabicyclo[2.2.1]heptane.

Most of the compounds of this invention have at least one asymmetric centre and often more than one; and can therefore exist both as enantiomers and as diastereoisomers. In particular, those compounds possessing an unsymmetrical azabicyclic ring system may exist as exo and endo diastereoisomers. It is to be understood that the invention covers all such isomers and mixtures thereof.

Also included within the scope of the present invention are salts of the novel compounds. It will be appreciated that salts of the compounds for use in medicine will be non-toxic pharmaceutically acceptable salts. Other salts may, however, be useful for the preparation of the compounds of the invention or their non-toxic pharmaceutically acceptable salts. Acid addition salts, for example, may be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Where the novel compound carries a carboxylic acid group the invention also contemplates salts thereof, preferably non-toxic pharmaceutically acceptable salts thereof, such as the sodium, potassium and calcium salts thereof.

Salts of amine groups may also comprise the quaternary ammonium salts in which the amino nitrogen atom carries an alkyl, alkenyl, alkynyl or aralkyl group. Such quaternary ammonium derivatives penetrate poorly into the central nervous system and are therefore useful as peripherally selective muscarinic agents, useful for example as antispasmodic agents, agents to reduce gastric acid secretion, agents to block the muscarinic actions of acetylcholinesterase inhibitors in the treatment of myasthenia gravis and as agents to co-administer with muscarinic agonists in Alzheimer's disease.

The method of treatment of this invention includes a method of treating Alzheimer's disease, senile dementia of the Alzheimer type, Huntington's chorea, tardive dyskinesia, hyperkinesia, mania or Tourette syndrome by the administration to a patient in need of such treatment of an effective amount of one or more of the novel compounds.

This invention therefore also provides a pharmaceutical composition comprising a compound of the invention and a pharmaceutically acceptable carrier.

It may, where appropriate, be advantageous, in order to reduce unwanted peripherally mediated side-effects, to incorporate into the composition a peripherally acting cholinergic antagonist (or antimuscarinic agent). Thus the compounds of the invention may advantageously be administered together with a peripheral cholinergic antagonist such as N-methylscopolamine, N-methylatropine, propantheline, methantheline or glycopyrrolate.

The compounds of the invention can be administered orally, parenterally or rectally at a daily dose of about 0.01 to 10 mg/kg of body weight, preferably about 0.1 to 1 mg/kg, and may be administered on a regimen of 1–4 times a day. When a cholinergic antagonist is administered, it is incorporated at its conventional dose.

The pharmaceutical formulations of this invention preferably are in unit dosage forms such as tablets, pills, capsules, powders, granules, sterile parenteral solutions or suspensions, or suppositories for oral, parenteral or rectal administration. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills or capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups and flavoured emulsions with edible oils such as cottonseed oil, sesame oil, coconut oil and peanut oil, as well as elixirs and similar pharmaceutical vehicles. Suitable dispersing or suspending agents for aqueous suspension include synthetic and natural gums such as tragacanth, acacia, alginate, dextran, sodium carboxymethylcellulose, methylcellulose, polyvinyl-pyrrolidone and gelatin.

The compounds of this invention may be prepared by a process which comprises the dehydroxylation or decarboxylation of a compound of formula III or a salt thereof:

wherein V represents a pyrazine, pyridazine or pyrimidine ring, independently substituted on each of the remaining ring carbon atoms with a substituent of low lipophilicity or a hydrocarbon substituent; A represents the residue of an azacyclic or azabicyclic ring; and B represents hydroxy or carboxy.

When the group B in compound III is hydroxy, it may be removed by chlorination and elimination, followed by hydrogenation. For example, chlorination and elimination may be effected by treatment with phosphorus oxychloride in the presence of triethylamine, or with thionyl chloride followed, where necessary, by DBN. The chloride or the unsaturated product may then be hydrogenated under conventional conditions, such as over 10% palladium/carbon in methanol. Alternatively, the compound III may be dehydroxylated by the use of thionyl chloride followed by treatment with tributyltin hydride in a solvent such as tetrahydrofuran in the presence of a radical initiator such as azabisisobutyronitrile.

The compound of formula III where B is hydroxy may be prepared by reaction of a ketone compound of formula IV with a metal derivative of a pyrazine, pyridazine or pyrimidine of formula V:

wherein A and V are as defined above; and M represents a metal atom, for example lithium. The lithium derivative for instance may be prepared by reacting the corresponding iodo-substituted pyrazine, pyridazine or pyrimidine with t-butyl lithium.

When the group B in compound III is carboxy it may be removed by standard decarboxylation techniques such as heating in aqueous solution made to pH1 with hydrochloric acid.

The compounds of formula III where B represents carboxy may be prepared by reaction of a compound of formula VI with a compound of formula VII:

wherein $R^1$ and V are as defined above, Hal represents halogen, and W represents cyano, a carboxylic acid group or a derivative thereof which activates the adjacent position; and subsequently converting the group W to carboxy, preferably by hydrolysis.

Preferably W represents an alkyl ester group such as methoxycarbonyl. Preferably the halogen group is iodide. The reaction between compounds VI and VII may be carried out in the presence of a strong base such as lithium diisopropylamide in a solvent such as tetrahydrofuran.

The azacyclic or azabicyclic moiety may be introduced into the molecules concerned by methods known from the art, in particular by methods analogous to those described in EP-A-0239309.

After any of the above described processes is complete, one substituent can be converted to another. For example an amino group may be converted to chloro, or hydrazo, —NHNH$_2$, via the intermediacy of diazonium, —N$_2$. Similarly, a chloro substituent may be converted to methoxy by reaction with a nucleophile such as methoxide; alkoxycarbonyl groups may be converted, via carboxy, to an amino substituent, —NH$_2$; and methoxy may be converted to hydroxy by treatment with concentrated hydrobromic acid.

In any of the above reactions it may be necessary and/or desirable to protect any sensitive groups in the compounds. For example, if the reactants employed include amino, carboxy, keto, hydroxy or thiol groups, these may be protected in conventional manner. Thus, suitable protecting groups for hydroxy groups include silyl groups such as trimethylsilyl or t-butyldimethylsilyl, and etherifying groups such as tetrahydropyranyl; and for amino groups include benzyloxycarbonyl and t-butoxycarbonyl. Keto groups may be protected in the form of a ketal. Carboxy groups are preferably protected in a reduced form such as in the form of their corresponding protected alcohols, which may be subsequently oxidised to give the desired carboxy group. Thiol groups may be protected by disulphide formation, either with the thiol itself or with another thiol to form a mixed disulphide. The protecting groups may be removed at any convenient stage in the synthesis of the desired compound according to conventional techniques.

The following Examples illustrate the preparation of compounds according to the invention. Each of the compounds of the Examples demonstrates an affinity for the muscarinic receptor, having an IC$_{50}$ (concentration required to displace 50% of specific [$^3$H]N-methylscopolamine binding from rat cortical membrane preparations) significantly lower than 100 μM. Penetrability into the central nervous system of compounds of this invention was assessed by a measurable displacement of radioligand binding using standard "exvivo" binding techniques (Ref: *J. Neurosurg.*, 1985, 63, 589-592).

In the Examples, all temperatures are in °C.; THF is tetrahydrofuran; and ether is diethyl ether.

EXAMPLE 1

3-(2-Pyrazinyl)-1-azabicyclo2.2.2]octan-3-ol t-Butyllithium (11.43 ml of a 1.4M solution in hexane, 16 mmol) was added dropwise to a rapidly stirred solution of 2-iodopyrazine (Hirschberg et al. *J. Org. Chem.*, (1961), 26, 1907: 1.65 g, 8.0 mmol) in ether (60 ml). at −35° C. After 0.25 h a solution of quinuclidinone (1 g, 8.0 mmol) in ether (20 ml) was added dropwise and the reaction mixture warmed to room temperature and stirred for 2 h. Quenching with water (25 ml) was followed by extracting with dichloromethane (4×75 ml) and drying (Na$_2$SO$_4$). The residue remaining after evaporation of the solvents under reduced pressure was purified by chromatography on alumina (Grade II-III), using dichloromethane/methanol (93:7) as eluant, to give 3-(2-pyrazinyl)-1-azabicyclo[2.2.2]octan-3-ol as a red solid (0.5 g). The product was further purified by recrystallisation from ethyl acetate, m.p. 187°-190° C. (dec); (Found C, 64.24; H, 7.34; N, 20.68. C$_{11}$H$_{15}$N$_3$O requires C, 64.39; H, 7.32: N, 20.49%); δ (360 MHz, CDCl$_3$) 1.20-1.40 (1H m, CH of CH$_2$); 1.50-1.70 (2H, m, CH$_2$); 2.10-2.25 (1H, m, CH of CH$_2$): 2.34 (1H, b rs, CH); 2.70-2.80 (2H, m, CH$_2$—N); 2.88-3.00 (3H, m, CH$_2$—N and CH of CH$_2$—N); 3.85 (1H, dd, J=1.5 and 16 Hz, CH of CH$_2$—N); 4.85 (1H, br s, OH); 8.54 (1H, d, J=2 Hz, pyrazine-H); 8.65 (1H, d, J=2 Hz, pyrazine-H); 8.89 (1H, d, J=2 Hz, pyrazine-H).

EXAMPLE 2

3-(2-Pyrazinyl)-1-azabicyclo[2.2.2]octane. Hydrochloride

Thionyl chloride (0.24 g. 1.55 mmol) was added dropwise to a rapidly stirred solution of 3-(2-pyrazinyl)-1-azabicyclo[2.2.2]octan-3-ol (0.21 g, 1.02 mmol) in dichloromethane (10 ml) at −5° C. The reaction mixture was warmed to room temperature and then refluxed for 3 h. Water (5 ml) was added to the solution, basified to pH >10 with potassium carbonate and extracted with dichloromethane (3×50 ml). The combined extracts were dried (Na$_2$SO$_4$), the solvent removed under vacuum and the residue chromatographed through alumina (Grade II-III) using dichloromethane/methanol (98:2) as eluant to give 3-(2-pyrazinyl)-1-azabicyclo[2.2.2]oct-2-ene as a pale yellow solid (0.14 g), δ (360 MHz, CDCl$_3$) 1.54-1.61 (2H, m, CH$_2$); 1.77-1.95 (2H, m, CH$_2$); 2.63-2.71 (2H, m, CH$_2$—N); 3.02-3.09 (2H, m, CH$_2$—N); 3.53-3.56 (1H, m, CH-bridgehead); 7.30 (1H, d, J=1.5 Hz vinyl-H); 8.41 (1H, d, J=2 Hz, pyrazine-H); 8.52 (1H, dd, J=1 and 2 Hz, pyrazine-H) 8.78 (1H, d, J=1 Hz, pyrazine-H).

A solution of 3-(2-pyrazinyl)-1-azabicyclo [2.2.2]oct-2-ene (75 mg, 0.4 mmol), in ethanol (20 ml), was hydrogenated over 10% pd/C (75 mg) in a Parr apparatus. After 1.5 h the catalyst was removed by filtration through hyflo and the solvent removed under reduced pressure. Chromatography of the residue through alumina eluting with dichloromethane/methanol (95:5) gave 3-(2-pyrazinyl)-1-azabicyclo [2.2.2]octane (55 mg) as a pale yellow oil. The hydrochloride salt was prepared, m.p. 203°-205° C. (isopropyl alcohol/ether); (Found C, 55.23; H, 7.15; N, 17.86 C$_{11}$H$_{15}$N$_3$. HCl. 0.75 H$_2$O requires C, 55.23; H, 7.32: N, 17.57%); m/e 189 (M$^+$ for free base); δ (360 MHz, D$_2$O) 1.70-1.85 (2H, m, CH$_2$); 2.10-2.30 (2H, m, CH$_2$); 2.40-2.48 (1H, m, CH-bridgehead); 3.28-4.04 (7H, m, 3×CH$_2$ and CH); 8.52 (1H, m, pyrazine-H); 8.63 (2H, m, pyrazine-H).

EXAMPLE 3

3-[2-(6-Methylpyrazin)yl]-1-azabicyclo[2.2.2]octan-3-ol t-Butyllithium (11.43 ml of a 1.4M solution in hexane, 16 mmol) was added dropwise to a rapidly stirred solution of 2-methyl-6-iodopyrazine (Spoerri et al; *J. Am. Chem. Soc.*, (1952), 74, 1580; 1.76 g, 8 mmol) in ether (50 ml) at −35° C. After 0.25 h a solution of quinuclidinone (1 g, 8.0 mmol) in ether (20 ml) was added dropwise and the reaction mixture warmed to room temperature and stirred for 2.5 h. Water (15 ml) was added and the mixture extracted with dichloromethane (4×75 ml). The combined extracts were dried (Na$_2$SO$_4$) and the residue remaining after evaporation of the solvent was chromatographed on alumina using dichloromethane/methanol (90:10) as eluant to give 3-[2-(6-methylpyrazin)yl]-1-azabicyclo[2.2.2]octan-3-ol (0.45 g) as an orange oil which crystallised on standing, m.p. 182°-184° C.

(ethylacetate/ether); (Found C, 64.63; H, 7.72; N, 18.13. $C_{12}H_{17}N_3O \cdot 0.25\ H_2O$ requires C, 64.40; H, 7.88; N, 18.77%); m/e 219 (M+ for free base); δ (360 MHz, D$_2$O) 1.28-1.40 (1H, m, CH of CH$_2$); 1.56-1.72 (2H, m, CH$_2$); 2.12-2.22 (1H, m, CH of CH$_2$); 2.37 (1H, br s, CH-bridgehead); 2.60 (3H, s, Me); 2.76-2.80 (2H m CH$_2$); 2.88-3.06 (3H, m, CH$_2$ and CH of CH$_2$); 3.90 (1H, d J=14.5 Hz, CH of CH$_2$); 8.40 (1H, s, pyrazine-H); 8.64 (1H, s, pyrazine-H).

EXAMPLE 4

3-[2-(6-Methylpyrazin)yl]-1-azabicyclo[2.2.2]octane Hydrogen Oxalate

Thionyl chloride (0.38 ml) was added dropwise to a rapidly stirred solution of 3-[2-(6-methylpyrazin) yl]-1-azabicyclo[2.2.2]octan-3-ol (0.35 g, 1.6 mmol) in dichloromethane (15 ml) at 0° C. The reaction mixture was warmed to room temperature and stirred for 2 h. Water (5 ml) was added and then basified to PH >10 with potassium carbonate. The aqueous was extracted with dichloromethane (3×75 ml), the combined extracts dried (Na$_2$SO$_4$) and the residue remaining, after removal of solvents, chromatographed through alumina using ethyl acetate as eluant, to give a mixture of 3-chloro-3-[2-(6-methylpyrazin)yl]1-azabicyclo[2.2.2]octane and 3-[2-(6-methylpyrazin) yl]-1-azabicyclo[2.2.2]oct-2-ene (0.26 g) which was taken through to the final Product without separation.

A solution of the above mixture (0.28 g) in ethanol (25 ml) was hydrogenated over 10% Pd/C (0.2 g) in a Parr apparatus. After 1.5 h the catalyst was removed by filtration through hyflo and the solvent removed under reduced pressure. The crude product was purified by chromatography through alumina using dichloromethane/methanol (93:7) as eluant to give the title-pyrazine as a yellow oil (0.22 g). The hydrogen oxalate salt was prepared. m.p. 184.5°-186° C. (isopropyl alcohol); (Found C, 57.49, H, 6.45; N, 14.63. $C_{12}H_{17}N_3 \cdot C_2H_2O_4$ requires C, 57.32; H, 6.52; N, 14.32%); m/e 203 (M+ for free base); δ (360 MHz, D$_2$O) 1.78-1.85 (2H, m, CH$_2$); 2.10-2.20 (2H, m, CH$_2$); 2.42-2.44 (1H, m, CH); 2.57 (3H, s, Me); 3.30-3.89 (6H, m, 3×CH$_2$—N); 4.01-4.05 (1H, m, C$\underline{H}$-pyrazine); 8.38 (1H, s, pyrazine-H); 8.42 (1H, s, pyrazine-H).

EXAMPLE 5

3-[2-(6-Methoxypyrazin)yl]-1-azabicyclo[2.2.2]octane. Dihydrochloride 1. 2-Methoxy-6-iodopyrazine 2,6-Dichloropyrazine (20 g, 134 mmol) was added to a saturated solution of sodium iodide in water (12 ml) and butan-2-one (800 ml). A mixture of hydroiodic acid (18 ml) and Water (24 ml) was added and the dark red solution refluxed for 4.5 days. The residue remaining after removal of the solvent was taken up into water (75 ml). sodium metabisulphite (0.4 g) added, and the solution basified with sodium hydroxide. The aqueous was extracted with dichloromethane (3×150 ml). the combined extracts dried (Na$_2$SO$_4$) and the solvent removed in vacuo. The solid obtained after cooling overnight was filtered off, washed with petroleum ether, and dried under vacuum to give 2,6-diiodopyrazine (7.15 g) which was used directly in the next stage.

2,6-Diiodopyrazine (6.06 g, 18.2 mmol) was added to a solution of sodium (0.42 g, 18.2 mmol) in methanol (45 ml) and heated under reflux for 3.5 h. Water (150 ml) was added and extracted With ether (3×150 ml). The combined extracts were dried (Na$_2$SO$_4$) and the residue remaining after removal of the solvent was chromatographed through silica gel eluting with ether/petroleum ether (50:50) to give 2-methoxy-6-iodopyrazine (4.17 g); δ (360 MHz, CDCl$_3$) 3.95(3H,s,OMe); 8.18(1H,s,pyrazine-H); 8.45(1H,s,pyrazine-H).

2. 3-[2-(6-Methoxypyrazin)yl]-1-azabicyclo[2.2.2]octan-3-ol t-Butyllithium (20 ml of a 1.7M solution in pentane, 35.3 mmol) was added dropwise to a rapidly stirred solution of 2-methoxy-6-iodopyrazine (4.17 g, 17.6 mmol) in ether (80 ml), at −40° C. After 0.25 h a solution of quinuclidinone (2.21 g, 17.6 mmol) in ether (60 ml) was added dropwise and the reaction mixture warmed to room temperature and stirred for 2 h. Water (35 ml) was added and extracted with ethylacetate (4×100 ml). The combined extracts were dried (Na$_2$SO$_4$), the solvent removed under vacuum and, the residue chromatographed through alumina, eluting with dichloromethane/methanol (93:7) to give 3-[2-(6-methoxypyrazin)yl]-1-azabicyclo [2.2.2]octan-3-ol (1.65 g); δ (360 MHz, CDCl$_3$) 1.37-1.51 (3H,m, —CH$_2$ and CH of CH$_2$); 1.70-1.90(1H, brs, OH); 1.94-1.96-(1H,m,CH); 2.20-2.32(1H,m,CH of CH$_2$); 2.80-3.10(5H,m,2×CH$_2$ and CH of CH$_2$) 3.74(1H,dd, J=2 and 14.6 Hz, CH of CH$_2$); 3.99(3H,s,Me); 8.15(1H,s,pyrazine-H); 8.39(1H,s,pyrazine-H).

3. 3-[2-(6-Methoxypyrazin)yl]-1-azabicyclo[2.2.2]octane Dihydrochloride

Thionyl chloride (2.83 g, 23.8 mmol) was added dropwise to a rapidly stirred solution 3-[2-(6-methoxypyrazin)yl]-1-azabicyclo[2.2.2]octan-3-ol (1.87 g, 7.9 mmol) in dichloromethane (80 ml), at 0° C. The solution was warmed to room temperature and stirred for 19 h. The solvent and excess thionyl chloride were removed under vacuum, the residue taken up into water (30 ml) and basified with potassium carbonate. The aqueous was extracted with dichloromethane (4×75 ml). the combined extracts dried (Na$_2$SO$_4$) and the solvent removed under vacuum. Chromatography of the residue through alumina, eluting with ethyl acetate gave a mixture of 3-chloro-3-[2-(6-(methoxypyrazin)yl]-1-azabicyclo[2.2.2]octane and 3-[2-(6-methoxypyrazin)yl]-1-azabicyclo [2.2.2]oct-2-ene (1.1 g).

A solution of the above mixture (1.1 g) in methanol (25 ml) was hydrogenated over 10% Pd/C (0.11 g) in a Parr apparatus. After 5 h the catalyst was removed by filtration through hyflo and the solvent removed under reduced pressure. The dihydrochloride salt was prepared, m.p. 161°-163° C. (isopropylalcohol/ether); (Found C,48.48; H,6.60; N,14.03. $C_{12}H_{17}N_3O \cdot 2HCl \cdot 0.2H_2O$ requires C,48.71; H,6.56; N,14.21%); m/e 219(M+ for free base); δ (360 MHz D$_2$O)1.72-2.40(5H,m,2×CH$_2$ and CH); 3.30-3.75(6H,m,3×CH$_2$—N); 4.04(3H,s,OMe); 4.01-4.08(1H,m,CH); 8.13(1H,s,pyrazine-H); 8.16(1H,s,pyrazine-H).

EXAMPLE 6

3-[2-(6-Hydroxypyrazin)yl]-1-azabicyclo[2.2.2]octane. Dihydrobromide

A solution of 3-[2-(6-methoxy-pyrazin)yl]-1-azabicyclo[2.2.2] in concentrated hydrobromic acid (10 ml) was refluxed for 20 h. The acid was removed under vacuum and the residue triturated with ether. The solid obtained was recrystallised from methanol/ether m.p. 255°–258° C. (dec.); (Found C,36.15; H,4.74; N,11.20. $C_{11}H_{15}N_3O$. 2HBr requires C,35.99; H,4.67; N,11.45%). m/e 205 (M+ for free base). δ (360 MHz, $D_2O$) 1.79–2.45(5H,m,2×$CH_2$ and CH); 3.32–3.78(6H,m,3×$CH_2$—N); 7.72 (1H, s, pyrazine-H); 8.08 (1H, s, pyrazine-H).

EXAMPLE 7

3-(2-Pyrazinyl)-1-azabicyclo[2.2.1]heptan-3-ol t-Butyllithium (10.6 ml of a 1.7M solution in pentane, 18 mmol) was added dropwise to a rapidly stirred solution of 2-iodopyrazine (1.86 g, 9.0 mmol) in ether (50 ml), at −45° C. After 0.25 h a solution of 1-azabicyclo[2.2.1]heptan-3-one (1 g, 9.0 mmol) in ether (20 ml) was added dropwise and the reaction mixture warmed to room temperature and stirred for 16 h. Water (25 ml) was added and the solution stirred for 0.25 h before adding dichloromethane (150 ml) and extracting. The aqueous was extracted twice more with dichloromethane (2×150 ml). the extracts combined, dried ($Na_2SO_4.MgSO_4$) and the solvent removed under vacuum. The residue was purified by chromatography through alumina, eluting with dichloromethane/methanol (93:7). Recrystallisation from ethyl acetate gave 3-(2-pyrazinyl)-1-azabicyclo[2.2.1]heptan-3-ol (0.51 g) as a pale yellow solid, m.p. 180°–183° C.; (Found C, 62.10; H,6.79; N,21.48. $C_{10}H_{13}N_3O.0.15H_2O$ requires C,61.95; H,6.87; N,21.68%; δ (360 MHz,$CDCl_3$) 1.40–1.59(1H,m,CH of $CH_2$); 2.33–2.36(1H,m,CH of $CH_2$); 2.47(1H,dd,J=4 and 10 Hz, CH of $CH_2$—N); 2.59(1H,dd J=4 and 10 Hz, CH of $CH_2$—N); 2.74(1H,d, J=4Hz, CH-bridgehead); 2.76–2.81(1H,m,CH of $CH_2$—N); 2.93–3.03(2H,m,2×CH of 2×$CH_2$—N); 3.39(1H,dd J=1.5 and 15Hz, CH of $CH_2$—N); 4.10–4.30(1H,m,OH); 8.49–8.50(2H,m,pyrazine-H); 8.87(1H,m,pyrazine-H).

EXAMPLE 8

3-(2-Pyrazinyl)-1-azabicyclo[2.2.1]heptane. Dihydrochloride(Isomer B)

Thionyl chloride (1.5 g, 12.6 mmol) was added to a rapidly stirred solution of 3-(2-pyrazinyl)-1-azabicyclo[2.2.1]heptan-3-ol (0.5 g, 2.6 mmol) in dichloromethane (30 ml) at room temperature. The solution was stirred for 1 h, heated at 60° C. for 0.5 h, and then cooled to room temperature, before adding water (20 ml) and basifying with potassium carbonate. Extraction into dichloromethane (3×75 mls), drying ($Na_2SO_4$) and chromatography of the residue remaining after removal of solvent through alumina, using ethyl acetate as eluant, gave 3-chloro-3-(2-pyrazinyl)-1-azabicyclo[2.2.1]heptane as a pale yellow oil (0.18 g); m/e 209 (M+ of free base); δ (360 MHz,$CDCl_3$) 0.84–0.92(1H,m,CH of $CH_2$); 1.58–1.67(1H,m,CH of $CH_2$); 2.42–2.48(1H,m,CH of $CH_2$—N); 2.69–2.72(1H,m,CH of $CH_2$—N); 2.78–2.86(1H,m,CH of $CH_2$—N); 3.22–3.24(1H,d, J=4.5 Hz, CH-bridgehead); 3.42–3.49(2H,m,2×CH of $CH_2$—N); 4.13(1H,dd J=3 and 14 Hz, CH of $CH_2$); 8.48(2H,s,pyrazine-H); 8.91(1H,s,pyrazine-H).

A solution of 3-chloro-3-(2-pyrazinyl)-1-azabicyclo[2.2.1]heptane (0.18 g, 0.85 mmol) in methanol (30 ml) was hydrogenated over 10% pd/C (0.18 g) in a Parr apparatus. After 1 h the suspension was filtered through hyflo and the solvent removed under vacuum to give the title pyrazine as a cyrstalline solid (0.18 g). The dihydrochloride salt was prepared. m.p. 183°–186° C. (isopropyl alcohol/ether); (Found C,47.47; H,6.22,N,16.57. $C_{10}H_{13}N_3.2HCl.0.3H_2O$ requires C,47.36; H,6.16: N,16.51%); δ (360 MHz, $CDCl_3$, free-base); 1.64–1.92(2H,m,$CH_2$); 3.17–3.19(1H,m,CH-bridgehead); 3.30–3.37(2H,m,2×CH of $CH_2$—N); 3.48–3.59(2H,m,2×CH of $CH_2$—N); 3.82–3.84(2H,m,2×CH of $CH_2$); 3.96–4.00(1H,m,CH); 8.53–8.56(2H,m,pyrazine-H).

EXAMPLE 9

6-(2-Pyrazinyl)-1-azabicyclo[3.2.1]octan-6-ol t-Butyllithium (15.5 ml of a 1.7M solution in pentane, 26.3 mmol) was added dropwise to a rapidly stirred solution of 2-iodopyrazine (2.96 g), 14.3 mmol) in ether (70 ml), at −50° C. The brown suspension was stirred at −50° C. for 0.25 h and a solution of 1-azabicyclo[3.2.1]octan-6-one (1.5 g, 11.9 mmol) in ether (30 ml) then added dropwise. The reaction mixture was warmed to room temperature and stirred for 6.25 h before adding water (10 ml) and extracting with ethyl acetate (3×100 ml). The crude product was chromatographed through alumina using dichloromethane/methanol (90:10) as eluent to give the title-pyrazine alcohol as a pale yellow solid (0.48 g). m.p. 208°–210° C. (ethanol); (Found C,64.04; H,7.38; N,20.25. $C_{11}H_{15}N_3O$ requires C,64.36; H,7.36; N,20.47%): m/e 205 (M+); δ (360 MHz, $D_2O$) 1.57–2.34(4H,m,2×$CH_2$); 2.50–2.54 (1H, m, CH-bridgehead); 2.90–3.21(5H,m,2×$CH_2$—N and 0.5×$CH_2$—N); 3.72(1H,d,J=14 Hz, 0.5×$CH_2$—N); 8.52(1H,d,J=2Hz,pyrazine-H); 8.56(1H,dd,J=1.2 and 2 Hz, pyrazine-H); 8.91(1H,d,J=1.2 Hz,pyrazine-H).

EXAMPLE 10

6-(2-Pyrazinyl)-1-azabicyclo[3.2.1]octane Dihydrochloride

Thionyl chloride (0.34 g, 2.92 mmol) was added dropwise to a rapidly stirred solution of 6-(2-pyrazinyl)-1-azabicyclo[3.2.1]heptan-6-ol (0.2 g, 0.97 mmol) in dichloromethane (15 ml), at 0° C. The solution was stirred for 16h at room temperature, the solvents removed under vacuum and the residue taken up into water (10 ml) and basified with potassium carbonate. The residue obtained after extraction, into dichloromethane (3×50 ml). drying ($Na_2SO_4$) and evaporation, was chromatographed through alumina, using ethyl acetate as eluant, to give 6-chloro-6-(2-pyrazinyl)-1-azabicyclo[3.2.1]octane as a yellow solid (0.10 g); δ (60 MHz, $CHCl_3$)1.20–1.80(4H,m,2×$CH_2$) 2.70–3.70(6H,m,2×$CH_2$—N) 0.5×$CH_2$—N, and CH); 4.50(1H,dd,J=3 and 14 Hz,0.5×$CH_2$); 8.50(2H,s,pyrazine-H); 8.82(1H,s,pyrazine-H).

Tributyltinhydride (0.24 ml, 0.88 mmol) was added to a stirred solution of 6-chloro-6-(2-pyrazinyl)1-azabicyclo[3.2.1]octane (0.14 g, 0.63 mmol) in THF (75 ml). Azoisobutyronitrile (AIBN) (0.1 g) was added and the mixture heated rapidly to reflux. After 1.5 h and 7.75 h further portions of AIBN (50 mg) were added followed by a second Portion of tributyltinhydride (0.24 ml, 0.88 mmol) and refluxed for a further 4 h. The reaction mixture was allowed to cool overnight, dichloromethane (50 ml) added and the basic products extracted into 2N hydrochloric acid (3×25 ml). The combined acid washings were basified with potassium carbonate and extracted with dichloromethane (4×75 ml). The combined extracts were dried (Na$_2$SO$_4$) and evaporated, and the residue purified by alumina chromatography using dichloromethane/methanol (95:5) as eluant to give the title-pyrazine as a yellow solid (0.05 g). The dihydrochloride salt was prepared, m.p. 268°–271° C. (dec.); (Found C,49.13; H,6.49; N,15.57. C$_{11}$H$_{15}$N$_3$.2HCl.0.35H$_2$O requires C,49.20; H,6.60; N,15.65%); m/e 189(M+ for free base); δ (CDCl$_3$) 1.38–1.84(4H,m,2×CH$_2$); 3.16–4.26(8H,m,3×CH$_2$ and 2×CH); 8.54(1H, d,J=2 Hz, pyrazine-H); 8.62(1H,dd,J=1.5 and 2 Hz, pyrazine-H); 8.70(1H,d,J=1.5Hz, pyrazine-H).

EXAMPLE 11

3-(5-Pyrimidinyl)-1-azabicyclo[2.2.2]octan-3-ol n-Butyllithium (12 ml of a 1.6M solution in hexane 19.2 mmol), at −110° C., was added dropwise to a solution of 5-bromopyrimidine (2.0 g, 12.5 mmol) in THF (60 ml) and ether (60 ml), at −110° C. (ethanol/liquid nitrogen bath). The resultant yellow solution was stirred at −110° C. for 1.25 h and a solution of quinuclidinone (1.72 g, 13.75 mmol) in THF (20 ml) also at −110° C., added dropwise. The reaction mixture was stirred at −110° C. for 0.1 h then warmed to room temperature and stirred for 16 h. 2N-Hydrochloric acid (25 ml) was added and stirred for 0.25 h. The organic phase was washed with water (15 ml) and the combined aqueous extracts basified with potassium carbonate and extracted with dichloromethane (4×75 ml). Chromatography of the residue obtained upon removal of the solvents through alumina using dichloromethane/methanol (90:10) as eluant, gave 3-(5-pyrimidinyl)-1-azabicyclo[2.2.2]octan-3-ol as a yellow solid, m.p. 126°–127° C. (ethyl acetate/ether); (Found C,61.42; H,7.47; N,19.60. C$_{11}$H$_{15}$N$_3$O. 0.5H$_2$O requires C,61.66; H,7.53; N,19.61%); m/e 205(M+); δ (360 MHz,D$_2$O) 1.30–1.44(1H,m,0.5×CH$_2$); 1.65–1.74(2H,m,CH$_2$); 2.10–2.20(1H,m,0.5×CH$_2$); 2.30–2.32(1H,m,CH-bridgehead); 2.68–2.96(4H,m.2×CH$_2$); 3.09(1H,dd,J=1.5 and 14.7 Hz, 0.5×CH$_2$); 3.49(1H,dd,J=1.5 and 14.7 Hz,0.5×CH$_2$); 8.96(2H,s,pyrimidine-H); 9.08(1H,s,pyrimidine-H).

EXAMPLE 12

3-(5-Pyrimidinyl)-1-azabicyclo[2.2.2]octane. Hydrochloride

Thionyl chloride (0.35 ml. 4.8 mmol) was added to a rapidly stirred solution of 3-(5-pyrimidinyl)-1-azabicyclo[2.2.2] octan-3-ol (0.5 g, 2.4 mmol) in dichloromethane (15 ml), at 0° C. The solution was warmed to room temperature and stirred for 1 h before adding a second portion of thionyl chloride (0.2 ml) and refluxing for 0.25 h. The mixture was cooled to 10° C., water (10 ml) added and basified to pH >10 with potassium carbonate. Extraction into dichloromethane (3×50 ml). drying (Na$_2$SO$_4$) and evaporation of solvents under reduced pressure gave 3-(5-pyrimidinyl)-1-azabicyclo[2.2.2]oct-2-ene (0.16 g) as a yellow oil which crystallised on standing at 0° C., m/e 188 (M+H)+; δ (360 MHz,D$_2$O) 1.86–1.98 (2H, m,CH$_2$); 2.15–2.26(2H,m,CH$_2$); 3.18–3.30 (2H,m,0.5×CH$_2$ and CH); 3.62–3.72(3H,m,CH$_2$ and 0.5×CH$_2$) 7.23(1H,s,vinyl-H): 9.00(2H,s,pyrimidine-H); 9.15(1H,s,pyrimidine H). A solution of 3-(5-pyrmidinyl)-1-azabicyclo[2.2.2]oct-2-ene (0.31 g 1.66 mmol) in ethanol (40 ml) was hydrogenated over 10% pd/C (0.12 g) in a Parr apparatus. After 4 h the suspension was filtered through hyflo, the solvent removed under vacuum and, the residue chromatographed on alumina using dichloromethane/methanol (95:5) as eluant, to give 3-(5-pyrimidinyl)-1-azabicyclo[2.2.2]octane (0.17 g) as a yellow oil. The hydrochloride salt was made. m.p. 267°–270° C. (dec.); (Found C,56.00; H,6.88, N,17.74. C$_{11}$H$_{15}$N$_3$.HCl.0.75H$_2$O requires C,55.69; H,6.58; N,17.71%) m/e 189 (M+ for free base); δ (360 MHz,D$_2$O) 1.89–1.94(2H,m,CH$_2$); 2.13–2.24 (2H,m,CH$_2$); 2.38–2.46 (1H, m, CH-bridgehead); 3.34–3.90(7H,m,3×CH$_2$—N and CH); 8.85(2H,s,pyrimidine-H); 9.09 (1H,s,pyrimidine-H).

EXAMPLE 13

3-[5-(2-Methylpyrimidin)yl]-1-azabicyclo[2.2.2]octane. Dihydrochloride

1.

3-[5-(2-Methylpyrimidin)yl]-1-azabicyclo[2.2.2]octan-3-ol n-Butyllithium (12.2 ml of a 1.6 ml solution in hexane, 19.6 mmol), cooled to −100° C., was added dropwise to a solution of 2-methyl-5-bromo-1,3-pyrimidine (Kosolapoff et al, J. Org. Chem, (1960), 1898; 2.04 g, 11.8 mmol) in THF (61 ml) and ether (61 ml), at −105° C. (ethanol/liquid nitrogen bath). The yellow solution was stirred at −105° C. for 1 h before adding a solution of quinuclidinone (1.62 g, 12.9 mmol), in THF (21 ml), that had been precooled to −100° C. The reaction mixture was allowed to warm to room temperature over a period of 2.25 h. Workup with water (30 ml) and extraction into dichloromethane (3×100 ml) gave a crude product which was chromatographed through alumina, eluting with dichloromethane/methanol (93:7) to give the title-alcohol (0.57 g) as a pale yellow solid, m.p. 167° C. (ethyl acetate); (Found C,65.72; H,7.72; N,19.80. C$_{12}$H$_{17}$N$_3$O requires C,65.72, H,7.81; N,19.16%); 1.29–1.42 (1H, m, 0.5×CH$_2$); 1.60–1.74(2H,m,CH$_2$); 2.26–3.32(1H,m,CH-bridgehead); 2.70(3H,s,Me); 2.70–3.00(4H,m,2×CH$_2$); 3.06 (1H,d,J=15 Hz, 0.5×CH$_2$—N); 3.47(1H,d,J=15Hz, 0.5×CH$_2$—N); 8.83(2H,s,pyrimidine-H).

2.

3-[5-(2-Methylpyrimidin)yl]-1-azabicyclo2.2.2]octane. Dihydrochloride

Thionyl chloride (1.2 g) was added to a stirred solution of 3-[5-(2-methylpyrimidin)yl]-1-azabicyclo[2.2.2]octan-3-ol (0.57 g, 2.6 mmol) in dichloromethane (20 ml), at 0° C. The solution was warmed to room temperature and then refluxed for 16 h. Basic aqueous workup followed by extraction into dichloromethane gave a crude product which was chromatographed through alumina using dichloromethane/methanol, as eluant, to give 3-[5-(2-methylpyrimidin)yl]-1-azabicyclo[ 2.2.2]oct-2-ene (0.1 g) as a brown oil. A solution of 3-[5-(2-methylpyrimidin)yl]-1-azabicyclo[2.2.2]oct-2-ene (0.1 g, 0.5 mmol) in ethanol (15 ml) was hydrogenated over 10% of Pd/C (0.1 g) in a Parr shaker. After 16 h the catalyst was removed by filtration through hyflo and the solvent removed under vacuum to give 3-[5-(2-methylpyrimidin)yl]-1-azabicyclo-]2.2.2]octane(0.1 g) as a yellow oil. The dihydrochloride salt was prepared, m.p. 255.5°–257.5° C.; (Found C,51.58; H,6.91; N,15.47. C$_{12}$H$_{17}$N$_3$.2HCl requires C, 52.18: H,6.93; N,15.21%); m/e 203 (M+ for free base); δ (360 MHz,D$_2$O) 1.84–1.94 (2H, m, CH$_2$); 2.06–2.27 (2H, m, CH$_2$); 2.32–2.44 (1H, m, CH-bridgehead);

2.78(3H,s,Me); 3.32–3.92(7H,m, 3×CH$_2$—N and CH); 8.90 (2H, s, pyrimidine-H).

EXAMPLE 14

3-(2-Pyrazinyl)-1-azabicyclo[2.2.1]heptane. Hydrochloride(Isomer A)

Sodium methoxide (1 g, 18.5 mmol) was added portionwise to a rapidly stirred solution of 3-(2-pyrazinyl)-1-azabicyclo[2.2.1]heptane(Isomer B) (0.3 g, 1.7 mmol). in methanol (20 ml) and heated at 65° C. for 24 h. The solvents were removed under vacuum, the residue taken up into dichloromethane (1.5 ml) and chromatographed through alumina using dichloromethane/methanol (98.5:1.5) as eluant to give the title pyrazine (0.2 g) as a single isomer. The compound was further purified as the hydrochloride salt, m.p. 172°–175° C. (isopropyl alcohol/ether); (Found C, 52.00; H, 6.36; N, 18.01. C$_{10}$H$_{13}$N$_3$. 1.5 HCl requires C, 52.23; H, 6.31; N, 18.28%) δ (360 MHz, D$_2$O) 1.99–2.06 (1H, m, CH of CH$_2$); 2.19–2.29 (1H, m, CH of CH$_2$); 3.17–3.20 (2H, m, 2×CH); 3.35–3.42 (1H, m, CH of CH$_2$); 3.48–3.57 (1H, m, CH of CH$_2$); 3.62–3.71 (3H, m, CH and CH$_2$); 3.91–3.97 (1H, m, CH); 8.52 (1H, d, J=2 Hz, pyrazine-H); 8.64 (2H, s, 2×pyrazine H).

EXAMPLE 15 exo-3-(2-Pyrazinyl)-1-azabicyclo[2.2.1]heptan-5-ol

1. trans-3,4-Dicarbomethoxypyrrolidine

This was prepared from glycine and dimethylfumarate by the procedure reported by Joucla et al, *J. Chem. Soc. Chem. Commun.*, (1985), 1566.

2. 1-Carbomethoxymethyl-trans-3,4-dicarbomethoxypyrrolidine

A solution of trans-3,4-dicarbomethoxypyrrolidine (4.1 g, 22 mmol) in xylene (30 ml) was added to a rapidly stirred suspension of potassium carbonate (7 g) in xylene (150 ml) at 120° C. After 0.25 h, a solution of methylbromoacetate (3.45 g, 22.5 mmol) in xylene (30 ml) was added dropwise and the mixture stirred rapidly at 140° C. for 2 h. The solution was decanted from the inorganic residue which was taken up into water (100 ml) and extracted with dichloromethane (3×150 ml). The combined organics were dried (Na$_2$SO$_4$) and the solvent removed under vacuum to give the title triester as a yellow liquid (6 g); m/e 259 (M$^+$ for free base). (Found: M$^+$=259.1048; C$_{11}$H$_{17}$NO$_6$ requires M$^+$=259.1056); δ(360 MHz, CDCl$_3$) 2.96–3.11 (4H, m, 2×CH$_2$N); 3.34 (2H, AB q, J=16.5 Hz, CH$_2$CO$_2$Me); 3.46–3.52 (2H, m, 2×CH); 3.74 (9H, s, 3×$\overline{\text{CO}}_2$Me).

3. 3-Carbomethoxy-5,5-dimethoxy-1-azabicyclo[2.2.1]heptane

A solution of 1-carbomethoxymethyl-trans-3,4-dicarbomethoxypyrrolidine (5 g, 19.31 mmol) in toluene (75 ml) was added dropwise over a 1 h period to a rapidly stirred solution of potassium-t-butoxide (9 g, 80 mmol) in toluene (250 ml) at 130° C. The mixture was refluxed for 4 h, cooled to room temperature and concentrated hydrochloric acid (75 ml) added dropwise and stirred for 0.25 h. The organic phase was extracted with further portions of acid (3×50 ml) and the combined aqueous heated at 110° C. for 16 h. The solvent was then removed under vacuum, the residue dried and taken up into methanol (saturated with hydrogen chloride) (150 ml). The mixture was stirred at room temperature for 24 h and the solvent removed under vacuum. The residue was dissolved in water (50 ml), basified to pH >10 with potassium carbonate and extracted with dichloromethane (5×150 ml). The combined extracts were dried (Na$_2$SO$_4$) and the residue remaining after removal of solvents was chromatographed through silica-gel using dichloromethane/methanol (93:7) as eluant, to give the title ester as a yellow liquid (0.5 g). An analytical sample was prepared as the hydrogen oxalate salt, mp 134.5°–136.5° C. (isopropylalcohol); (Found: C, 47.04; H, 6.20, N, 4.50. C$_{10}$H$_{17}$NO$_4$. (CO$_2$H)$_2$ requires C, 47.21; H, 6.27; N, 4.59%); δ (360 MHz, CDCl$_3$) 2.44 (1H, dd, J=3 and 9.8 Hz, CH of CH$_2$—N); 2.63 (1H, dd, J=3 and 12.7 Hz, CH of CH$_2$—N); 2.77 (1H, d, J=12.7 Hz, CH of CH$_2$—N); 2.80–3.10 (5H, m, 2 of CH and 1.5 of CH$_2$); 3.11 (3H, s, OMe); 3.24 (3H, s, OMe); 3.71 (3H, s, CO$_2$Me).

4. 3-(2-Pyrazinyl)-3-carbomethoxy-5,5-dimethoxy-1-azabicyclo[2.2.1]heptane

Lithium diisopropylamide (3.7 ml of a 1.5M solution in THF, 5.58 mmol) was added dropwise to a solution of 3-carbomethoxy-5,5-dimethoxy-1-azabicyclo[2.2.1]heptane (1 g, 4.7 mmol) in THF (40 ml), at −78° C., and stirred for 2 h. A solution of 2-iodopyrazine (1.15 g, 5.58 mmol) in THF (5 ml) was added, at −78° C., stirred for 1 h, and then warmed to room temperature and stirred for 16 h. Water (25 ml) and dichloromethane (70 ml) were added and the aqueous extracted with dichloromethane (3×100 ml). The combined extracts were dried (Na$_2$SO$_4$), evaporated, and the crude product chromatographed through silica-gel using dichloromethane/methanol (92:8) as eluant to give the title compound as a yellow liquid (0.1 g); (Found: M$^+$=293.1378; C$_{14}$H$_{19}$N$_3$O$_4$ requires M$^+$=293.1376); m/e 293 (M$^+$); δ (360 MHz, CDCl$_3$) 2.34 (1H, d, J=16 Hz, CH of CH$_2$N); 2.82 (1H, s, CH-bridgehead); 3.05 (1H, dd, J=4.3 and 14.6 Hz, CH of $\overline{\text{CH}}_2$—N); 3.18 (3H, s, OMe); 3.20 (1H, dd, J=3.3 and 8.5 Hz, CH of CH$_2$—N); 3.28 (1H, d, J=12.7 Hz, CH of CH$_2$—N); 3.34 (3H, s, OMe); 3.59 (3H, s, CO$_2$Me); 3.67 (1H, d, J=10.8 Hz, CH of CH$_2$—N); 3.91 (1H, dd, J=3 and 12.7 Hz, CH of CH$_2$—N); 8.45 (1H, d, J=3.7 Hz, pyrazine-H); 8.51 (1H, dd, J=2.5 and 3.7 Hz, pyrazine-H); 8.58 (1H, d, J=2.5 Hz, pyrazine-H).

5. exo-3-(2-Pyrazinyl)-5,5-dimethoxy-1-azabicyclo[2.2.1]heptane

Sodium hydroxide (2.5 ml of a 6N solution) was added to a solution of the preceding ester (0.1 g, 0.34 mmol) in methanol (1 ml) and heated at 70° C. for 24 h. The solution was cooled to room temperature and concentrated hydrochloric acid added until the solution was pH1 (≃1 ml) and stirred at room temperature for 16 h. The reaction mixture was basified to pH 10 with potassium carbonate and extracted with dichloromethane (3×50 ml). The combined extracts were dried (Na$_2$SO$_4$), evaporated, and the residue (60 mg) taken up into methanol (1 ml) and sodium methoxide (50 mg, 0.9 mmol) added. The solution was heated at 65° C. for 18 h, the solvent removed under vacuum and the residue chromatographed through alumina using dichloromethane/methanol (98:2) as eluant to give exo-3-(2-pyrazinyl)-5,5-dimethoxy-1-azabicyclo[2.2.1]heptane (45 mg); (Found: (M+H)=236.1394; $C_{12}H_{17}N_3O_2$ requires (M+H)$^+$=236.1399); m/e 236 (M+H)$^+$; (360 MHz, CDCl$_3$) 2.46 (1H, d, J=15 Hz, 0.5 of CH$_2$N); 2.86 (1H, s, CH-bridgehead); 2.90-3.20 (5H, m, 2.5 of CH$_2$N); 3.24 (3H, s, OMe); 3.32 (3H, s, OMe); 3.40-3.50 (1H, m, CH-pyrazine); 8.40 (1H d, J=1.5 Hz, pyrazine-H); 8.46-8.52 (2H, m, 2 of pyrazine-H).

6. exo-3-(2-Pyrazinyl)-1-azabicyclo[2.2.1]heptan-5-one

A solution of exo-3-(2-pyrazinyl)-5,5-dimethoxy-1-azabicyclo[2.2.1]heptane (50 mg, 0.2 mmol) in perchloric acid (3 ml of a 70% solution in water) was heated at 65° C. for 2 h. Dichloromethane (30 ml) was added to the reaction mixture followed by water (5 ml) and basified with sodium carbonate. The aqueous was extracted into dichloromethane (4×50 ml), dried (Na$_2$SO$_4$) and evaporated, to give the ketone (35 mg) m/e 189 (M$^+$); δ(360 MHz, CDCl$_3$) 2.95 (1H, dd, J=4.2 and 17.8 Hz, CH of CH$_2$—N); 3.08 (1H, d, J=11.3 Hz, CH of CH$_2$—N); 3.10 (1H, s, CH-bridgehead); 3.10-3.53 (5H, m, 2 of CH$_2$—N and CH-pyrazine); 8.45-8.54 (3H, m, 3 of pyrazine-H).

7. exo-3-(2-Pyrazinyl)-1-azabicyclo[2.2.1]heptan-5-ol

Sodium borohydride (25 mg, 0.6 mmol) was added to a stirred solution of the preceding ketone (35 mg, 0.18 mmol) in ethanol (3 ml), at 10° C. After 0.5 h the solution was warmed to room temperature and stirred for a further 0.5 h. Excess borohydride was destroyed with 2N hydrochloric acid and the solvents then removed under vacuum. The residue was taken up into water (5 ml), basified with potassium carbonate and extracted into dichloromethane (3×25 ml). The combined extracts were dried (Na$_2$SO$_4$) and the solvent removed under vacuum to give exo-3-(2-pyrazinyl-1-azabicyclo[2.2.1]heptan-5-ol as a crystalline solid (20 mg), m.p. 198°-201° C. (isopropylalcohol); (Found: C, 62.61; H, 6.87; N, 21.79. $C_{10}H_{13}N_3O$ requires C, 62.81; H, 6.85; N, 21.97%): m/e 191 (M$^+$); δ(360 MHz, CDCl$_3$) 1.90 (1H, br s, OH); 2.18 (1H, m, CH of CH$_2$—N); 2.60 (1H, d, J=10.2 Hz, CH of CH$_2$—N); 2.79 (1H, d, J=4.3 Hz, CH-bridgehead); 3.04 (1H, dd, J=3.5 and 10 Hz, CH of CH$_2$—N); 3.13-3.26 (3H, m, 1.5 of CH$_2$—N); 3.79-3.82 (1H, m, CH-pyrazine); 4.49-4.53 (1H, m, CH—OH); 8.39 (1H, s, pyrazine-H); 8.49 (2H, s, 2 of pyrazine-H).

EXAMPLE 16

3-Fluoro-3-(2-pyrazinyl)-1-azabicyclo2.2.1]heptane Hydrochloride

Diethylaminosulphur trifluoride (0.42 g, 2.62 mmol) was added to a stirred solution of 3-(2-pyrazinyl)-1-azabicyclo[2.2.1]heptan-3-ol (0.5 g, 2.62 mmol) in dichloromethane (30 ml), at −65° C. After 24 h, water (20 ml) was added, basified with potassium carbonate, and extracted into dichloromethane (3×50 ml). The combined extracts were dried (Na$_2$SO$_4$), evaporated, and the residue chromatographed through silica-gel, eluting with dichloromethane-methanol (90:10) to give 3-fluoro-3-(2-pyrazinyl)-1-azabicyclo[2.2.1]heptane (75 mg). The compound was further purified as the hydrogen chloride salt, m.p. 245° C. (dec.) (isopropylalcohol); (Found: C, 52.33; H, 5.79; N, 17.97. $C_{10}H_{12}F.HCl$ requires C, 52.29; H, 5.66; N, 18.30%) m/e 193 (M$^+$ for free base); δ(360 MHz, CDCl$_3$) 1.06-1.13 (1H, m, CH of CH$_2$—N); 1.44-1.55 (1H, m, CH of CH$_2$—N); 2.58 (1H, dd, J=3.1 and 9.7 Hz, CH of CH$_2$—N); 2.65-2.72 (1H, m, CH of CH$_2$—N); 2.83-2.91 (2H, m, CH-bridgehead and CH of CH$_2$—N); 3.09-3.24 (2H, m, 2 of CH of CH$_2$—N); 3.59 (1H, ddd, J=3.1, 13.6 and 20.8 Hz, CH of CH$_2$—N); 8.50-8.53 (2H, m, 2 of pyrazine-H); 8.91 (1H, d, J=1.2 Hz, pyrazine-H).

EXAMPLE 17

1-Methyl-3-(2-pyrazinyl)pyrrolidine Hydrogen Oxalate 1. 1-methyl-3-carbomethoxypyrrolidine A solution of sarcosine (30 g, 0.34 mol), methylacrylate (29 g, 0.34 mol) and paraformaldehyde (20.2 g, 0.67 mol) in toluene (3 l) was refluxed in a Dean-Stark trap apparatus for 0.5 h. The reaction mixture was cooled to room temperature and stirred for 16 h. Filtration through cotton wool and concentration under vacuum gave the title ester as a pale yellow liquid (21 g) m/e 143 (M$^+$); δ(250 MHz, CDCl$_3$) 2.05-2.16 (2H, m, CH$_2$); 2.36 (3H, s, N—Me); 2.48-2.84 (4H, m, 2 of CH$_2$—N); 2.98-3.10 (1H, m, CH—CO$_2$Me); 3.70 (3H, s, CO$_2$Me).

2. 1-Methyl-3-carbomethoxy-3-(2-pyrazinyl)pyrrolidine

A solution of lithium diisopropylamide in anhydrous THF was prepared by addition of n-butyllithium (7.9 ml of a 1.6M solution in hexane, 12.64 mmol) to a solution of diisopropylamine (1.4 g, 13.9 mmol) in THF (200 ml), at −78° C. The solution was stirred for 0.5 h before adding dropwise to a stirred solution of 1-methyl-3-carbomethoxypyrrolidine (1.5 g, 10.5 mmol) in THF (200 ml), at −78° C. After 1 h, a solution of 2-iodopyrazine (2.73 g, 13.3 mmol) in THF (10 ml) was added dropwise, at −78° C., stirred for 0.25 h, warmed to room temperature, and stirred for a further 16 h. Water (25 ml) and dichloromethane (150 ml) were added, stirred for 0.25 h before separating the aqueous and extracting into dichloromethane (3×100 ml). The combined extracts were dried (Na$_2$SO$_4$), concentrated under vacuum, and the residue purified by silica-gel chromatography using dichloromethane/methanol (92:8) as eluant. The title pyrazine was obtained as an orange oil (0.36 g) m/e 222 (M$^+$); δ(360 MHz, CDCl$_3$) 2.38 (3H, s, N—Me); 2.43-2.51 (1H, m, CH of CH$_2$); 2.66-2.92 (3H, m, CH of CH$_2$ and CH$_2$—N); 3.15 (1H, d, J=9.7 Hz, CH of CH$_2$—N) 3.33 (1H, d, J=9.7 Hz, CH of CH$_2$—N); 3.72 (3H, s, CO$_2$Me); 8.44 (1H, d, J=1.5 Hz, pyrazine-H); 8.49 (1H, d, J=2 Hz, pyrazine-H), 8.64 (1H, dd, J=1.5 and 2 Hz, pyrazine-H).

3. 1-Methyl-3(2-pyrazinyl)pyrrolidine. Hydrogen Oxalate

Sodium hydroxide (4 ml of a 2N solution) was added to a solution of the preceding ester (0.35 g, 1.5 mmol) in methanol (3 ml) and stirred at room temperature for 0.5 h. Concentrated hydrochloric acid (5 ml) was added to the reaction mixture and stirred at room temperature for 16 h. The methanol was removed under vacuum, the aqueous basified to pH 10 with potassium carbonate and extracted with dichloromethane (4×100 ml). The residue remaining after drying (Na$_2$SO$_4$) and removal of solvents under vacuum was chromatographed on alumina (Grade II/III) using dichloromethane/methanol (98:2) as eluant to give the title -pyrazine (0.21 g). The hydrogen oxalate salt was prepared by addition of an ethereal solution of oxalic acid to a solution of the amine in ether, m.p. 142.5°-143° C. (isopropylacohol); (Found: C, 52.06; H, 5.99; N, 16.50. $C_9H_{13}N_3.(CO_2H)_2$ requires C, 52.17; H, 5.97; N, 16.59%); m/e 163 (M$^+$ for free base); δ(360 MHZ, D$_2$O) 2.16-2.77 (2H, m, CH$_2$); 3.03 and 3.06 (3H, s, N—Me); 3.27-3.58 (2H, m, CH$_2$—N);

3.82–4.13 (3H, m, CH$_2$—N and C$\underline{\text{H}}$-pyrazine); 8.50–8.64 (3H, m, 3 of pyrazine-H).

EXAMPLE 18

6-(2-Pyrazinyl)-1-azabicyclo[3.2.1]octane. Hydrogen Oxalate (Isomer B)

A solution of 6-(2-pyrazinyl)-1-azabicyclo[3.2.1]octane(Isomer A, Example 10) (0.7 g, 3.7 mmol) and sodium methoxide (1 g, 18.5 mmol) in methanol (8 ml) was heated at 120° C. with stirring, for 17 h. The solvent was removed under vacuum and the residue chromatographed through alumina (Grade II/III) using dichloromethane/methanol (95:5) as eluant to give 6-(2-pyrazinyl)-1-azabicyclo[3.2.1]octane(Isomer B) (0.69 g) as a white crystalline solid. The hydrogen oxalate salt was prepared. m.p. 157.5°–158.5° C. (isopropylalcohol/ether). (Found: C, 55.50; H, 6.14; N, 14.72. C$_{11}$N$_{15}$N$_3$. (CO$_2$H)$_2$.0.15H$_2$O requires C, 55.37; H, 6.18; N, 14.90%); m/e 190 (M+H$^+$)$^{30}$; δ(360 MHz, D$_2$O) 1.79–1.88 (1H, m, CH of CH$_2$); 1.95–2.00 (2H, m, CH$_2$) 2.11–2.24 (1H, m, CH of CH$_2$); 2.75–2.78 (1H, m, CH-bridgehead); 3.31 (1H, d, J=10.8 Hz, CH of CH$_2$—$\overline{\text{N}}$); 3.34–3.43 (2H, m, 2 of CH of CH$_2$—N); 3.72–3.76 (1H, m, CH of CH$_2$—N); 3.84–4.02 (3H, m, 3 of CH of CH$_2$—N); 8.49 (1H d, J=2.6 Hz, pyrazine-H); 8.60–8.62 (2H, m, 2 of pyrazine-H).

EXAMPLE 19

3-[2-(6-Methoxypyrazin)yl]-1-azabicyclo[2.2.1]heptane (Isomer A). Dihydrochloride 1. 3-[2-(6-Methoxypyrazin)yl]-3-hydroxy-1-azabicyclo-[2.2.1]heptane t-Butyllithium (24 ml of a 1.7M solution in pentane, 40.8 mmol) was added dropwise to a rapidly stirred solution of 2-iodo-6-methoxypyrazine (4.7 g, 19.9 mmol) in ether (125 ml), at −50° C. The reaction mixture was stirred for 0.25 h and a solution of 1-azabicyclo[2.2.1]heptan-3-one (2.86 g, 25.8 mmol) in ether (20 ml) (predried over MgSO$_4$), then added and warmed to room temperature. Aqueous workup and extraction into dichloromethane gave the crude product which was chromatographed on alumina using dichloromethane/methanol (96:4) as eluant to give the title alcohol (2.91 g) as a yellow oil; (Found: M$^+$=221.1166; C$_{11}$H$_{15}$N$_3$O$_2$ requires M$^+$=21.1164); m/e 221 (M$^+$); δ(250 MHz, CDCl$_3$) 1.46–1.62 (1H, m, CH of CH$_2$); 2.26–2.40 (1H, m, CH of CH$_2$); 2.50 (1H, dd, J=3.5 and 12 Hz, CH of CH$_2$—N); 2.60 (1H, dd, J=4.5 and 14 Hz, CH of CH$_2$—N); 2.72 (1H, d, J=4.5 Hz, CH-bridgehead); 2.74–3.06 (2H, m, CH$_2$—N); 3.07–3.14 (1H, m, CH of CH$_2$—N); 3.42 (1H, dd, J=1.5 and 14 Hz, CH of CH$_2$—N); 3.96 (3H, s, OMe); 8.13 (1H, s, pyrazine-H); 8.37 (1H, s, pyrazine-H).

2. 3-[2-(6-Methoxypyrazin)yl]-3-chloro-1-azabicyclo[2.2.1]heptane

This was prepared from 3-[2-(6-methoxypyrazin)yl]-3-hydroxy-1-azabicyclo[2.2.1]heptane (2.91 g, 13.2 mmol) using thionyl chloride (100 ml) as described in the procedure for Example 8. The product was purified by chromatography on alumina (Grade II/III) using ethyl acetate as eluant to give the title chloride (0.38 g); δ(360 MHz, CDCl$_3$) 0.93–1.06 (1H, m, CH of CH$_2$); 1.54–1.68 (1H, m, CH of CH$_2$); 2.32–2.52 (1H, m, CH of CH$_2$—N); 2.66 (1H, dd, J=3 and 10.5 Hz, CH of CH$_2$—N); 2.76–2.88 (1H, m, CH of CH$_2$—N); 3.18 (1H, d, J=4.5 Hz, CH-bridgehead); 3.35–3.50 (2H, m 2 of CH of CH$_2$—N); 3.97 (3H, s, OMe); 4.02 (1H, dd, J=3 and 14 Hz. CH of CH$_2$—N); 8.13 (1H, s, pyrazine-H); 8.42 (1H, s, pyrazine-H).

3. 3-[2-(6-Methoxypyrazin)yl]-1-azabicyclo[2.2.1]heptane(Isomer A) Dihydrochloride A solution of 3-[2-(6-methoxypyrazin)yl]-3-chloro-1-azabicyclo[2.2.1]heptane (0.38 g. 1.6 mmol) in methanol (30 ml) was hydrogenated over 10% Pd/C (0.15 g) in a Parr apparatus. After 1 h the catalyst was removed by filtration through hyflo filter aid and the solvent removed under vacuum. The residue was chromatographed on alumina using dichloromethane/methanol (99:1) as eluant to give 3-[2-(6-methoxypyrazin)yl]-1-azabicyclo[2.2.1]heptane (Isomer A) (0.16 g). The dihydrochloride salt was prepared. m.p. 154.4°–154.7° C. (isopropylalcohol/ether); (Found: C, 47.69; H, 6.32: N, 15.21. C$_{11}$H$_{15}$N$_3$O. 2HCl requires C, 47.49; H, 6.16; N, 15.11%); m/e 205 (M$^+$ for free base); δ(360 MHz, D$_2$O) 1.74–1.98 (2H, m, CH$_2$); 3.29–3.30 (1H, m, CH-bridgehead): 3.30–3.56 (4H, m, 2 of CH$_2$—N); 3.71–3.92 (2H, m, CH$_2$) 4.04 (3H, s, OMe); 4.02–4.07 (1H, m, CH-pyrazine); 8.15 (1H, s, pyrazine H); 8.40 (1H, s, pyrazine H).

EXAMPLE 20

3-[2-(6-Methoxypyrazin)yl]-1-azabicyclo[2.2.1]heptane (Isomer B) Hydrochloride A solution of 3-[2-(6-methoxypyrazin)yl]-1-azabicyclo[2.2.1]heptane (Isomer A, Example 19) (0.83 g, 4 mmol) and sodium methoxide (5.6 g, 0.10 mole) in methanol (7 ml) was heated at 120° C. for 24 h, with stirring. The solvent was removed under vacuum, the residue taken up into dichloromethane/methanol (90:10) (50 ml) and filtered through a pad of celite. The solvent was removed under vaccum and the crude product chromatographed through alumina, using dichloromethane/methanol (99:1) as eluant to give the title pyrazine (0.26 g). The hydrochloride salt was prepared. m.p. 205.5°–206.5° C. (isopropylalcohol/ether); (Found C, 50.80; H, 6.29; N, 15.99. C$_{11}$H$_{15}$N$_3$.O.1.5HCl requires C, 50.82; H, 6.35; N, 16.17%); m/e 205 (M$^+$ for free base); δ(360 MHz, D$_2$O) 1.96–2.00 (1H, m, CH of CH$_2$); 2.16–2.25 (1H, m, CH of CH$_2$); 3.05 (1H, d, J=4.2 Hz, CH-bridgehead): 3.19 (1H, d, J=10.1 Hz, CH of C$\overline{\text{H}}_2$—N); 3.33–3.38 (1H, m, CH of CH$_2$—N); 3.48–3.55 (2H, m, 2 of CH of CH$_2$); 3.60–3.67 (1H, m, CH of CH$_2$—N); 3.84 (1H, d, J=10 Hz, CH of CH$_2$—N); 3.90–4.00 (1H, m, C$\underline{\text{H}}$-pyrazine); 4.00 (3H, s, OMe); 8.11 (1H, s, pyrazine-H); 8.12 (1H, s, pyrazine-H).

EXAMPLE 21

3-[2-(3-Methylpyrazin)yl]-1-azabicyclo[2.2.2]octan-3-ol 1. 2-Hydroxy-3-methylpyrazine 2-Hydroxy-3-methylpyrazine was prepared from glyoxal and alanine amide hydrochloride by the procedure of Karmas and Spoerri, J. Am. Chem. Soc., 1952, 74, 1580

2. 2-Iodo-3-methylpyrazine

This was prepared from 2-hydroxy-3-methylpyrazine according to the procedure of Hirschberg and Spoerri, J. Org. Chem., 1961, 1907. The compound was obtained as a low melting solid m.p. 39°–40° C. (lit. m.p. 40°–41° C.).

3.

3-[2-(3-Methylpyrazin)yl]-1-azabicyclo[2.2.2]octan-3-ol t-Butyllithium (28.2ml of a 1.7M solution in pentane, 48 mmol) was added dropwise to a rapidly stirred solution of 2-iodo-3-methylpyrazine (5.3 g, 24.1 mmol) in ether (150 ml), at −40° C. After 0.25 h a solution of quinuclidinone (3 g, 24.0 mmol) in ether (25 ml) was added dropwise and the dark red reaction mixture warmed to room temperature and stirred for 2 h. The residue remaining after aqueous workup and extraction into dichloromethane was chromatographed through alumina using dichloromethane/methanol (93:7) as eluant to give the title-alcohol (1.45 g) as a crystalline solid, m.p. 182° C. (dec.); m/e 219 (M+); (Found: M+=219.1367.$C_{12}H_{17}N_3O$ requires M+=219.1372): δ(360 MHz, CDCl$_3$) 1.26–1.50 (3H, m, CH$_2$ and CH of CH$_2$); 2.14–2.21 (1H, m, CH of CH$_2$); 2.55 (1H, br s, bridgehead-H); 2.55–2.92 (5H, m, CH$_2$ and CH of CH$_2$); 2.75 (3H, s, Me); 3.79 (1H, dd, J=1.8 and 14 Hz, CH of CH$_2$); 8.28–8.30 (2H, m, pyrazine-H).

EXAMPLE 22

3-[2-(3-Methylpyrazin)yl]-3-chloro-1-azabicyclo[2.2.2]octane and 3-[2-(3-methylpyrazin)yl]-1-azabicyclo[2.2.2]oct-2ene. Sesquioxalate Thionyl chloride (1.6 g, 13.4 mmol) was added dropwise to a rapidly stirred solution of 3-[2-(3-methylpyrazin)yl]-1-azabicyclo[2.2.2]octan-3-ol (1.45 g, 6.62 mmol) in dichloromethane (40ml) at −5° C. The reaction mixture was warmed to room temperature, stirred for 1 h and then refluxed for 0.5 h. The solution was cooled to room temperature, water (20 ml) added and basified with potassium carbonate and the aqueous separated. The aqueous was further extracted with dichloromethane (4×100 ml), dried (Na$_2$SO$_4$), evaporated, and the residue chromatographed through alumina using ethyl acetate as eluant to give two separated components. The less polar component, identified as 3-[2-(3-methylpyrazin)yl]-3-chloro-1-azabicyclo[2.2.2]octane was obtained as a crystalline solid (0.45 g), m.p. 92°–95° C.; m/e 237 (M+); (Found: M+=237.1028.$C_{12}H_{16}N_3Cl$ requires M+=237.1033); δ(360 MHz, CDCl$_3$) 1.24–1.72 (3H, m, CH$_2$ and CH of CH$_2$); 2.33–2.40 (1H, m, CH of CH$_2$); 2.60–2.68 (2H, m, CH$_2$); 2.78 (3H, s, Me); 2.95–3.13 (3H, m CH$_2$ and CH-bridgehead); 3.71 (1H, d, J=15 Hz, CH of CH$_2$); 3.97 (1H, br d, J=15 Hz, CH of CH$_2$); 8.33–8.34 (1H, m, pyrazine-H); 8.39 (1H, d, J=1.4 Hz, pyrazine-H).

The more polar component, identified as the second title-compound (0.26 g) was further purified as the sesquioxalate salt. m.p. 176°–178° C. (isopropyl alcohol); (Found: C, 53.33; H, 5.38; N, 12.42. $C_{12}H_{15}N_3.1.5$ (CO$_2$H)$_2$ requires C, 53.57; H, 5.36; N, 12.50%); δ(360 MHz, D$_2$O) 1.96–2.02 (2H, m, CH$_2$); 2.17–2.21 (2H, m, CH$_2$); 2.66 (3H, s, Me); 3.27–3.34 (2H, m, CH$_2$); 3.59 (1H, br s, CH-bridgehead); 3.67–3.74 (2H, m, CH$_2$); 7.10 (1H, d, J=1.27 Hz, vinyl-H); 8.51–8.61 (2H, m, pyrazine-H).

EXAMPLE 23

3-[2-(3-Methylpyrazin)yl]-1-azabicyclo2.2.2]octane. Dihydrochloride

A solution of 3-[2-(3-methylpyrazin)yl]-3-chloro-1-azabicyclo[2.2.2]octane (0.45 g, 1.68 mmol), in ethanol (30 ml) was hydrogenated over 10% Pd/C (200 mg) in a Parr apparatus, for 0.5 h. The catalyst was removed by filtration through hyflo-filter aid and the solvent removed under vacuum to give 3-[2-(3-methylpyrazin)yl]-1-azabicyclo[2.2.2]octane (0.45 g). The compound was purified as the dihydrochloride salt, m.p. 206°–210° C. (dec.). (Found: C, 48.02 H, 7.24; N, 14.03.$C_{12}H_{17}N_3.2HCl$. 1.3H$_2$O requires C, 48.10 H, 7.21; N, 14.03%): m/e 203 (M+); δ (360 MHz, D$_2$O) 1.71–1.77 (2H, m, CH$_2$); 2.09–2.18 (2H, m, CH$_2$); 2.38–2.40 (1H, m, CH-bridgehead); 2.71 (3H, s, Me); 3.28–3.37 (1H, m, CH of CH$_2$); 3.43 (1H, d, J=8.2 Hz, CH of CH$_2$); 3.45 (1H, d, J=8.2 Hz, CH of CH$_2$); 3.54–3.63 (2H, m, CH$_2$); 3.95–4.00 (1H, m, CH of CH$_2$); 4.15 (1H, dd, J=6.2 and 12.8 Hz, CH-pyrazine); 8.45 (1H, d, J=3 Hz, pyrazine-H); 8.75–8.78 (1H, m, pyrazine-H).

EXAMPLE 24 exo-3-[2-(6-Methylpyrazin)yl]-1-azabicyclo[2.2.1]heptan-3-ol t-Butyllithium (21 ml of a 1.7M solution in pentane; 36 mmol) was added dropwise to a rapidly stirred solution of 2-iodo-6-methylpyrazine (3.96 g, 18 mmol; Lutz el al., *J. Org. Chem.*, 1964, 415) in ether (75 ml), at −35° C. After 0.25 h a solution of 1-azabicyclo[2.2.1]heptan-3-one (2 g, 18 mmol) in ether (10 ml) was added dropwise and the dark red reaction mixture allowed to warm to room temperature and stir for 16 h. The residue obtained by aqueous workup and extraction into dichloromethane was chromatographed through alumina using dichloromethane/methanol (90:10) as eluant to give exo-3-[2-(6-methylpyrazin)yl]-1-azabicyclo[2.2.1]heptan-3-ol (2.00 g) as an oil; m/e 205 (M+); (Found: M+=205.1242. $C_{11}H_{15}N_3O$ requires M+=205.1215); δ (360 MHz, CDCl$_3$) 1.49–1.58 (1H, m, CH of CH$_2$); 2.32–2.43 (1H, m, CH of CH$_2$); 2.50 (1H, dd, J=3.7 and 10.3 Hz, CH of CH$_2$); 2.56 (3H, s, Me); 2.62 (1H, dd, J=3.7 and 12.9 Hz, CH of CH$_2$); 2.69 (1H, d, J=3.8 Hz, CH-bridgehead); 2.78–2.84 (1H, m, CH of CH$_2$); 2.93–3.06 (2H, m, CH$_2$); 3.38 (1H, d, J=12.9 Hz, CH of CH$_2$); 8.38 (1H, s, pyrazine-H); 8.62 (1H, s, pyrazine-H).

EXAMPLE 25 endo-3-[2-(6-Methylpyrazin)yl]-3-chloro-1azabicyclo[2.2.1]heptane

Thionyl chloride (5 g, 42 mmol) was added dropwise to a rapidly stirred solution of the preceding alcohol (2 g, 10 mmol) in dichloromethane (50 ml) at 0° C. The solution was warmed to 60° C. and stirred for 0.5 h, before cooling to room temperature, adding water (20 ml), and basifying with potassium carbonate. The aqueous was extracted with dichloromethane (4×70 ml), dried (Na$_2$SO$_4$) and evaporated. Chromatography of the residue through alumina using dichloromethane as eluant gave the title chloride (0.37 g) as a yellow oil; m/e 223 (M+) (Found: M+=223.0875.$C_{11}H_{14}N_3Cl$ requires M+=223.0876); δ (360 MHz, CDCl$_3$) 0.86–0.93 (1H, m, CH of CH$_2$); 1.56–1.65 (1H, m, CH of CH$_2$); 2.38–2.50 (1H, m, CH of CH$_2$); 2.56 (3H, s, Me); 2.67 (1H, dd, J=3.3 and 9.7 Hz, CH of CH$_2$); 2.71–2.83 (1H, m, CH of CH$_2$); 3.22 (1H, d, J=4.5 Hz, CH-bridgehead); 3.39–3.46 (2H, m, CH$_2$); 4.12 (1H, dd, J=2.9 and 13.8 Hz, CH of CH$_2$); 8.34 (1H, s, pyrazine-H); 8.68 (1H, s, pyrazine-H).

EXAMPLE 26 endo-3-[2-(6-Methylpyrazin)yl]-1-azabicyclo[2.2.1]heptane. Dihydrochloride

A solution of endo-3-[2-(6-methylpyrazin)yl]-3-chloro-1-azabicyclo[2.2.1]heptane (0.37 g, 1.7 mmol) in methanol (50 ml) was hydrogenated over 10% Pd/C (0.15 g) in a Parr apparatus for 1 h. The catalyst was removed by filtration, the solvent removed under vacuum, and the residue chromatographed through alumina using dichloromethane/methanol (97:3) as eluant to give the title compound (0.11 g). The dihydrochloride salt was prepared. m.p. 200°–202° C. (isopropylalcohol); (Found: C, 49.55; H, 6.38; N, 15.63.$C_{11}H_{15}N_3$.2.1HCl requires C, 49.70; H, 6.48; N, 15.81%); δ (360 MHz, $D_2O$) 1.58–1.66 (1H, m, CH of $CH_2$); 1.91–2.00 (1H, m, CH of $CH_2$); 2.64 (3H, s, Me); 3.36–3.52 (4H, m, $CH_2$, CH of $CH_2$ and CH-bridgehead); 3.58 (1H, d, J=8.3 Hz, CH of $CH_2$); 3.78–3.92 (2H, m, $CH_2$); 4.11–4.15 (1H, m, CH-pyrazine); 8.48 (1H, s, pyrazine-H); 8.49 (1H, s, pyrazine-H).

EXAMPLE 27 exo-3-[2-(6-Methylpyrazin)yl]-1-azabicyclo[2.2.1]heptane. Sesquioxalate

Sodium methoxide (0.5 g, 13 mmol) was added to a solution of endo-3-[2-(6-methylpyrazin)yl]-1-azabicyclo[2.2.1]heptane (0.17 g, 0.76 mmol) in methanol (3 ml) and stirred at 65° C. for 18 h. The residue remaining after removal of solvent was chromatographed through alumina using dichloromethane/methanol (99.5:0.5) as eluant to give the title-pyrazine (0.09 g). The sesquioxalate salt was prepared. m.p. 144–147° C. (isopropylalcohol); (Found: C, 51.79; H, 5.60; N, 12.88.$C_{11}H_{15}N_3$.1.5 $(CO_2H)_2$ requires C, 51.85; H, 5.59; N,12.96%); δ (360 MHz, $D_2O$) 1.97–2.05 (1H, m, CH of $CH_2$); 2.19–2.28 (1H, m, CH of $CH_2$); 2.57 (3H, s, Me); 3.17–3.19 (2H, m, CH of $CH_2$ and CH-bridgehead); 3.34–3.41 (1H, m, CH of $CH_2$); 3.47–3.55 (1H, m, CH of $CH_2$); 3.58–3.70 (3H, m, $CH_2$ and CH of $CH_2$); 3.92–3.98 (1H, m, CH-pyrazine); 8.40 (1H, s, pyrazine-H); 8.42 (1H, s, pyrazine-H).

EXAMPLE 28 exo-3-[2-(6-Dimethylaminopyrazin)yl]-1-azabicyclo[2.2.1]heptan-3-ol

1. 2-Iodo-6-dimethylaminopyrazine

A solution of 2,6-diiodopyrazine (6 g, 18.1 mmol) in methanol (50 ml) and dimethylamine (40% aqueous solution, 200 ml) was heated at reflux for 1 h. The methanol was removed under vacuum, the aqueous saturated with potassium carbonate and extracted with dichloromethane (3×100 ml). The combined extracts were dried ($Na_2SO_4$), evaporated and the residue purified by chromatography through silica-gel eluting with dichloromethane. The product (4 g) was obtained as a low melting solid, m.p. 46°–48° C., m/e 249 ($M^+$); δ (360 MHz, $CDCl_3$) 3.10 (6H, s, 2×Me); 7.87 (1H, s, pyrazine-H); 8.01 (1H, s, pyrazine-H).

2. exo-3-[2-(6-Dimethylaminopyrazin)yl]-1-azabicyclo[2.2.1]heptan-3-ol

The title-compound was prepared from 1-azabicyclo[2.2.1]heptan-3-one (1.6 g, 14.4 mmol) and 2-iodo-6-dimethylaminopyrazine (3.5 g, 14.1 mmol) by the procedure described for Example 1. The crude product was chromatographed through alumina using dichloromethane/methanol (96:4) as eluant to give the title-alcohol (1.55 g), m.p. 149°–150° C. (ethyl acetate); (Found: C, 61.26; H 7.72; N, 23.83. $C_{12}H_{18}N_4O$ requires C, 61.52; H, 7.74; N, 23.91%); m/e 234 ($M^+$); δ (360 MHz, $CDCl_3$) 1.46–1.56 (1H, m, CH of $CH_2$); 2.10 (1H, br s, OH); 2.32–2.38 (1H, m, CH of $CH_2$); 2.48 (1H, dd, J=3.6 and 10 Hz, CH of $CH_2N$); 2.58 (1H, dd, J=3.6 and 13 Hz, CH of $CH_2N$); 2.65 (1H, d, J=3.6 Hz, CH-bridgehead); 2.76–2.83 (1H, m, CH of $CH_2N$); 2.94–3.01 (1H, m, CH of $CH_2N$); 3.09 (1H, d, J=10 Hz, CH of $CH_2N$); 3.16 (6H, s, 2×NMe); 3.35 (1H, dd, J=2 and 13 Hz, CH of $CH_2N$); 7.95 (1H, s, pyrazine-H); 8.00 (1H, s, pyrazine-H).

EXAMPLE 29 endo-3-[2-(6-Dimethylaminopyrazin)yl]-1-azabicyclo[2.2.1]heptane. Dihydrochloride

1. endo-3-[2-(6-Dimethylaminopyrazin)yl]-3-chloro-1-azabicyclo[2.2.1]heptane Thionyl chloride (0.9 g, 7.6 mmol) was added dropwise to a solution of exo-3-[2-(6-dimethylaminopyrazin)yl]-1-azabicyclo[2.2.1]heptan-3-ol (1.25 g, 5.34 mmol) in dichloromethane (30 ml), at 0° C. The solution was warmed to room temperature, stirred for 1 h then warmed to 60° C. for 0.5 h. Water (5 ml) was added, basified with potassium carbonate and extracted with ethyl acetate (4×75 ml). The residue remaining after removal of solvent under vacuum was chromatographed through alumina using ethyl acetate as eluant to give the title-chloride (0.37 g), m.p. 90°–92° C.; m/e 252 ($M^+$); δ (360 MHz, $CDCl_3$) 1.01–1.08 (1H, m, CH of $CH_2$); 1.53–1.62 (1H, m, CH of $CH_2$); 2.40–2.46 (1H, m, CH of $CH_2N$); 2.65 (1H, dd, J=2.7 and 9.7 Hz, CH of $CH_2N$); 2.76–2.83 (1H, m, CH of $CH_2N$); 3.13 (6H, s, 2×NMe); 3.15 (1H, d, J=4.5 Hz, CH-bridgehead); 3.37–3.42 (2H, m, $CH_2N$); 4.09 (1H, dd, J=2.8 and 13.7 Hz, CH of $CH_2N$); 7.89 (1H, s, pyrazine-H); 8.10 (1H, s, pyrazine-H).

2. endo-3-[2-(6-Dimethylaminopyrazin)yl]-1-azabicyclo[2.2.1]heptane. Dihydrochloride A solution of the preceding chloride (0.47 g, 1.86 mmol) in ethanol (25 ml) was hydrogenated over 10% Pd/C (200mg) in a Parr apparatus for 1 h. The solvent removed under vacuum and the residue chromatographed through alumina using dichloromethane/methanol as eluant to give the title-compound (0.12 g). The dihydrochloride salt was prepared, m.p. 215°–217° C. (isopropyl alcohol/ether). (Found: C, 46.74; H, 6.95; N, 17.75. $C_{12}H_{18}N_4$. 2.5HCl requires C, 46.58: H, 6.67; N, 18.10%); m/e 218 ($M^+$); δ (360 MHz, $D_2O$) 1.74–1.81 (1H, m, CH of $CH_2$); 1.91–1.99 (1H, m, CH of $CH_2$); 3.22 (6H, s, 2×NMe); 3.29–3.32 (1H, m, CH-bridgehead); 3.37–3.43 (4H, m, 2 of $CH_2N$); 3.69–3.76 (1H, m, CH of $CH_2N$); 3.90–3.96 (1H, m, CH of $CH_2$); 4.02–4.07 (1H, m, CH-pyrazine); 7.77 (1H, s, pyrazine-H); 7.99 (1H, s, pyrazine-H).

EXAMPLE 30 exo-3-[2-(6-Dimethylaminopyrazin)yl]-1-azabicyclo[2.2.1]heptane. Dihydrochloride A solution of endo-3-[2-(6-dimethylaminopyrazin)yl]-1-azabicyclo[2.2.1]heptane (0.28 g, 1.28 mmol) and sodium methoxide (0.4 g, 74.0 mmol) in methanol (4 ml) was refluxed for 18 h. The solvent was removed under vacuum, the residue taken up into dichloromethane and chromatographed through alumina eluting with dichloromethane/methanol (98:2) to give the exo-diastereoisomer (60 mg). The dihydrochloride salt was prepared m.p. 217°-220° C. (isopropylalcohol/ether); (Found: C, 47.08: H, 6.75: N, 18.08. $C_{12}H_{18}N_4 \cdot 2.4HCl$ requires C, 47.13; H, 6.72; N, 18.32%); m/e 218 (M+); δ (360 MHz, $D_2O$) 1.96-2.01 (1H, m, CH of $CH_2$); 2.16-2.26 (1H, m, CH catalyst was removed by filtration through hyflo, the of $CH_2$); 3.11 (1H, d, J=4.3 Hz, CH-bridgehead); 3.19 (6H, s, 2×NMe): 3.20 (1H, d, J=7.3 Hz, CH of $CH_2N$); 3.32-3.40 (1H, m, CH of $CH_2N$); 3.47-3.65 (3H, m, $CH_2N$ and CH of $CH_2N$); 3.76 (1H, d, J=8.0 Hz, CH of $CH_2N$); 3.96-4.02 (1H, m, CH-pyrazine); 7.75 (1H, s, pyrazine-H); 7.97 (1H, s, pyrazine-H).

EXAMPLE 31 exo-3-[2-(6-Ethoxypyrazin)yl]-1-azabicyclo2.2.1]heptan-3-ol. Hydrochloride 1. 2-Iodo-6-ethoxypyrazine 2,6-Diiodopyrazine (12 g, 36.14 mmol) was added to a solution of sodium (0.83 g, 36.10 mmol) in ethanol (75 ml). The solution was refluxed for 1 h, the solvent removed under vacuum, water (40 ml) added and extracted into dichloromethane (4×200 ml). The solvent was removed under vacuum and the residue chromatographed through silica-gel using dichloromethane as eluant to give 2-iodo-6-ethoxy pyrazine (6.5 g). m.p. 36°-37° C.; δ (60 MHz, $CDCl_3$) 1.30 (3H, t, J=7 Hz, Me); 4.35 (2H, q, J=7 Hz, $CH_2Me$); 8.07 (1H, s, pyrazine-H): 8.35 (1H, s, pyrazine-H).

2. exo-3-[2-(6-Ethoxypyrazin)yl]-1-azabicyclo [2.2.1]heptan-3-ol. Hydrochloride

The title-alcohol was prepared from 1-azabicyclo[2.2.1]heptan-3-one (2.0 g, 18.0 mmol) and 2-iodo-6-ethoxypyrazine (4.50 g, 18.0 mmol) by the procedure described for Example 1. The crude product was chromatographed through alumina using dichloromethane/methanol (96:4) as eluant to give the title-alcohol (2.3 g). The hydrochloride salt was prepared. m.p. 235°-237° C. (isopropyl alcohol); (Found: C, 52.78: H, 6.72; N, 14.91. $C_{12}H_{17}N_3O_2 \cdot HCl \cdot 0.15H_2O$ requires C, 52.52; H, 6.72; N, 15.31%); m/e 235 (M+) δ (360 MHz, $D_2O$) 1.46 (3H, t, J=7.1 Hz, Me); 2.09-2.19 (1H, m, CH of $CH_2$); 2.56-2.64 (1H, m, CH of $CH_2$); 3.28 (1H, br s, CH-bridgehead); 3.28-3.31 (1H, m, CH of $CH_2N$); 3.35 (1H, dd, J=2.5 and 9.4 Hz, CH of $CH_2N$); 3.42-3.50 (1H, m, CH of $CH_2N$); 3.59-3.67 (1H, m, CH of $CH_2N$); 3.91 (1H, d, J=9.4 Hz, CH of $CH_2N$); 4.30 (1H, dd, J=2.5 and 12.4 Hz, CH of $CH_2N$); 4.47 (2H, q, J=7.1 Hz, $CH_2Me$); 8.17 (1H, s, pyrazine-H); 8.44 (1H, s, pyrazine-H).

EXAMPLE 32 endo-3-[2-(6-Ethoxypyrazin)yl]-1-azabicyclo[2.2.1]heptane. Sesquioxalate 1. endo-3-[2-(6-Ethoxypyrazin)yl]-3-chloro-1-azabicyclo[2.2.1]heptane The title-chloride was prepared from exo-3-[2-(6-ethoxypyrazin)yl]-1-azabicyclo[2.2.1]heptan-3-ol (2.30 g, 9.8 mmol) using the procedure described for Example 8. The crude product was chromatographed through alumina using ethyl acetate as solvent. The product (1.7 g) was obtained as an orange oil, m/e 254 (M+1)+; δ (360 MHz, $CDCl_3$) 0.96-1.04 (1H, m, CH of $CH_2$); 1.44 (3H, t, J=7.1 Hz, Me); 1.57-1.66 (1H, m, CH of $CH_2$); 2.38-2.46 (1H, m, CH of $CH_2N$); 2.66 (1H, dd, J=3.2 and 10.3 Hz, CH of $CH_2$); 2.78-2.86 (1H m, CH of $CH_2$); 3.19 (1H, d, J=4.5 Hz, CH-bridgehead); 3.37-3.41 (1H, m, CH of $CH_2N$): 3.44 (1H, dd, J=2.1 and 13.7 Hz, CH of $CH_2N$); 3.98 (1H, dd, J=2.8 and 13.7 Hz, CH of $CH_2N$); 4.40 (2H, q, J=7.1 Hz, $CH_2Me$); 8.10 (1H, s, pyrazine-H); 8.41 (1H, s, pyrazine-H).

2. endo-3-[2-(6-Ethoxypyrazin)yl]-1-azabicyclo[2.2.1]heptane. Sesquioxalate

The preceding chloride (1.7 g, 6.71 mmol) was hydrogenated over 10% Pd/C (0.5 g) as described for Example 8. The crude product was chromatographed through alumina using dichloromethane/methanol (99.5:0.5) as eluant to give the title-endo-pyrazine as the more polar of two components (0.5 g). The sesquioxalate salt was prepared m.p. 136°-137° C. (isopropyl alcohol). (Found: C, 50.79; H, 5.68; N, 11.86; $C_{12}17N_3O \cdot 1.5 (CO_2H)_2$ requires C, 50.85; H, 5.69; N, 11.86%): m/e 219 (M+); δ (360 MHz, $D_2O$) 1.41 (3H, t, J=6.84 Hz, Me); 1.72-1.82 (1H, m, CH of $CH_2$); 1.86-1.98 (1H, m, CH of $CH_2$); 3.27-3.29 (1H, m, CH-bridgehead); 3.36-3.55 (4H, m, 2 of $CH_2N$); 3.69-3.77 (1H, m, CH of $CH_2N$); 3.83-3.88 (1H, m, CH of $CH_2N$); 4.00-4.08 (1H, m, CH-pyrazine); 4.47 (2H, q, J=6.84 Hz, $CH_2Me$); 8.09 (1H, s, pyrazine-H); 8.12 (1H, s, pyrazine-H).

EXAMPLE 33 exo-3-[2-(6-Ethoxypyrazin)yl]-1-azabicyclo[2.2.1]heptane. Hydrochloride

The less polar product isolated from the chromatography of Example 32 part b was identified as the title-exo-pyrazine (0.10 g). The hydrochloride salt was prepared, m.p. 252°-253° C. (isopropyl alcohol); (Found: C, 56.14; H, 7.07; N, 16.35. $C_{12}H_{17}N_3O \cdot HCl$ requires C, 56.36; H, 7.09; N, 16.43%); m/e 219 (M+); δ (360 MHz, $D_2O$) 1.42 (3H, t, J=7.2 Hz, Me); 1.97-2.04 (1H, m, CH of $CH_2$); 2.17-2.27 (1H, m, CH of $CH_2$); 3.11 (1H, d, J=4.3 Hz, CH-bridgehead); 3.21 (1H, d, J=9 Hz, CH of $CH_2N$); 3.34-3.42 (1H, m, CH of $CH_2N$); 3.50-3.58 (2H, m, $CH_2N$); 3.62-3.69 (1H, m, CH of $CH_2N$); 3.83 (1H, d, J=9 Hz, CH of $CH_2N$); 3.88-3.94 (1H, m, CH-pyrazine); 4.46 (2H, q, J=7.2 Hz, $CH_2Me$); 8.09 (1H, s, pyrazine-H); 8.12 (1H, s, pyrazine-H).

EXAMPLE 34 endo-6-[2-(6-Methoxypyrazin)yl]-1-azabicyclo[3.2.1]octane. Dihydrochloride 1. exo-6-[2-(6-Methoxypyrazin)yl-1-azabicyclo[3.2.1]octan-6-ol The title-alcohol was prepared from 2-iodo-6-methoxypyrazine (4 g, 17.0 mmol) and 1-azabicyclo[3.2.1]octan-6-one (2.2 g, 17.6 mmol) using the procedure described for Example 1. The crude product was purified by chromatography through alumina, using dichloromethane/methanol (93:7) as eluant. The product (1 g) was obtained as a low melting solid, m.p. 43°-45° C. δ (360 MHz, $CDCl_3$) 1.44-1.51 (1H, m, CH of CH$_2$); 1.74-1.83 (1H, m, CH of CH$_2$) 1.89 (1H, br s, OH); 2.06-2.16 (1H, m, CH of CH$_2$); 2.11 (1H, d, J=3.6 Hz, CH-bridgehead); 2.32-2.43 (1H, m, CH of CH$_2$); 2.89 (1H, dd, J=3.1 and 12.0 Hz, CH of CH$_2$N); 2.96-3.08 (2H, m, CH$_2$N); 3.10 (1H, dd, J=3.1 and 13.7 Hz, CH of CH$_2$N); 3.34-3.38 (1H, m, CH of CH$_2$N); 3.61 (1H, d, J=13.7 Hz, CH of CH$_2$N); 3.97 (3H, s, OMe); 8.14 (1H, s, pyrazine-H); 8.36 (1H, s, pyrazine-H).

2.
endo-6-[2-(6-Methoxypyrazin)yl-6-chloro-1azabicyclo-[3.2.1]octane

The title-chloride was prepared from the preceding alcohol (1.0 g, 4.3 mmol) using the procedure described for Example 8. Chromatography through alumina using ethyl acetate as solvent gave the desired product (0.64 g), as a pale yellow oil, δ (360 MHz, CDCl$_3$) 1.07-1.16 (2H, m, CH$_2$); 1.62-1.82 (2H, m, CH$_2$); 2.80-2.90 (3H, m, CH$_2$N and CH-bridgehead); 3.07 (1H, dd, J=2.3 and 11.5 Hz, CH of CH$_2$N); 3.59-3.62 (1H, m, CH of CH$_2$N) 3.73 (1H, d, J=14.6 Hz, CH of CH$_2$N); 4.02 (3H, s, OMe); 4.44 (1H, dd, J=2.3 and 14.6 Hz, CH of CH$_2$N); 8.15 (1H, s, pyrazine-H); 8.41 (1H, s, pyrazine-H).

3.
endo-6-[2-(6-Methoxypyrazin)yl]-1-azabicyclo[3.2.-1]octane. Dihydrochloride A solution of the above chloride (0.64 g, 2.52 mmol) in ethanol (30 ml) was hydrogenated over 10% Pd/C (0.4 g) for 1 h. The product remaining after removal of catalyst and evaporation of solvent was chromatographed through alumina using dichloromethane/methanol (96:4) as eluant to give the title-endopyrazine as the more polar of two separated components (0.26 g). The dihydrochloride salt was prepared, m.p. 169°-170° C. (isopropyl alcohol/ether), (Found: C, 48.40; H, 6.36; N, 14.11. C$_{12}$H$_{17}$N$_3$O. 2HCl.0.2H$_2$O requires C, 48.72; H, 6.61; N, 14.20%); m/e 219 (M+); δ (360 MHz, D$_2$O) 1.46-1.57 (1H, m, CH of CH$_2$); 1.60-1.83 (2H, m, CH$_2$); 1.96-2.10 (1H, m, CH of CH$_2$); 3.06-3.12 (1H, m, CH-bridgehead); 3.36-3.50 (3H, m, CH$_2$N and CH of CH$_2$N); 3.62-3.66 (1H, m, CH of CH$_2$N); 3.94 (1H, dd, J=11.8 and 12.0 Hz, CH of CH$_2$N); 4.06 (3H, s, OMe); 4.12-4.19 (1H, m, CH of CH$_2$N); 4.27 (1H, ddd, J=1.8, 7.0 and 12.0 Hz, ); 8.17 (1H, s, pyrazine-H); 8.21 (1H, s, pyrazine-H).

EXAMPLE 35
exo-6-[2-(6-Methoxypyrazin)yl]-1-azabicyclo[3.2.1]octane. Hydrochloride The less polar product isolated from the chromatography of Example 34 part 3 was identified as the title exo-pyrazine (40 mg). The hydrochloride salt was prepared, m.p. 193°-196° C. (isopropyl alcohol/ether), (Found: C, 53.07: H 6.72; N, 15.40. C$_{12}$H$_{17}$N$_3$O. 1.4HCl requires C, 53.32; H, 6.86; N, 15.54%); m/e 219 (M+); δ (360 MHz, D$_2$O) 1.76-1.88 (1H, m, CH of CH$_2$); 1.90-2.02 (2H, m, CH of CH$_2$); 2.07-2.24 (1H, m, CH of CH$_2$); 2.73 (1H, br s, Ce,uns/H/-bridgehead); 3.32 (1H, d, J=10.9 Hz, CH of CH$_2$N); 3.38-3.42 (2H, m, 2×CH of CH$_2$N); 3.76 (1H, dd, J=6.0 and 8.0 Hz, CH of CH$_2$N); 3.82-3.94 (3H, m, 2×CH of CH$_2$N and CH-pyrazine); 4.00 (3H, s, OMe); 8.11 (1H s, pyrazine-H); 8.13 (1H, s, pyrazine-H).

EXAMPLE 36
endo-3-[2-(6-isopropoxypyrazin)yl]-1-azabicyclo[2.2.1]heptane. Hydrochloride

1. 2-Iodo-6-isopropoxypyrazine 2,6-Diiodopyrazine (8.72 g, 26.3 mmol) was added to a solution of sodium (0.61 g, 26.5 mmol) in isopropyl alcohol (75 ml). The solution was refluxed for 1 h, the solvent removed under vacuum, water (50 ml) added, and extracted into dichloromethane (4×200 ml). The residue remaining after removal of solvent under vacuum was chromatographed through silica-gel eluting with dichloromethane to give the title-pyrazine (4.56 g), δ (60 MHz, CDCl$_3$) 1.32 (6H, d, J=7 Hz, 2×Me); 5.23 (1H, m, CH(Me)$_2$); 8.00 (1H, s, pyrazine-H); 8.30 (1H, s, pyrazine-H).

2.
exo-3-[2-(6-isopropoxypyrazin)yl]-1-azabicyclo[2.2.1]heptan-3-ol

The title-alcohol was prepared from 1-azabicyclo[2.2.1]heptan-3-one (1.92 g, 17.3 mmol) and 2-iodo-6-isopropoxypyrazine (4.56 g, 17.3 mmol) using the procedure described for Example 1. The crude product was purified by chromatography through alumina eluting with dichloromethane/methanol (97:3). The product (2.0 g) was obtained as a viscous oil. (Found: M+ =249.1470. C$_{13}$H$_{19}$N$_3$O$_2$ requires M+ =249.14772); 1.38 (3H, d, J=5.4 Hz, Me); 1.39 (3H, d, J=5.4 Hz, Me); 1.50-1.58 (1H, m, CH of CH$_2$); 1.88 (1H, br s, OH); 2.29-2.40 (1H, m CH of CH$_2$); 2.51 (1H, dd, J=3.7 and 10.0 Hz, CH of CH$_2$N); 2.61 (1H, dd, J=3.7 and 12.8 Hz, CH of CH$_2$N); 2.72 (1H, d, J=3.7 Hz, CH-bridgehead); 2.76-2.86 (1H, m, CH of CH$_2$N); 2.96-3.06 (1H, m, CH of CH$_2$N); 3.11 (1H, d, J=10.0 Hz, CH of CH$_2$N); 3.41 (1H, dd, J=1.9 and 12.8 Hz, CH of CH$_2$N); 5.26 (1H, m, CH(Me)$_2$); 8.07 (1H, s, pyrazine-H); 8.32 (1H, s, pyrazine-H).

3.
endo-3-[2-(6-isopropoxypyrazin)yl]-3-chloro-1-azabicyclo[2.2.1]heptane The title-chloride was prepared from the preceding alcohol (1.0 g, 4.0 mmol) using the procedure described for Example 8. The product (0.6 g) was obtained as a yellow oil after chromatography through alumina using ethyl acetate as eluant, m/e 267 (M+); δ (360 MHz, CDCl$_3$) 0.98-1.06 (1H, m, CH of CH$_2$); 1.37 (3H, d, J=5.2 Hz, Me); 1.38 (3H, d, J=5.2 Hz, Me); 1.57-1.67 (1H, m, CH of CH$_2$); 2.37-2.45 (1H, m, CH of CH$_2$N); 2.66 (1H, dd J=3.2 and 10.3 Hz, CH of CH$_2$N); 2.78-2.86 (1H, m, CH of CH$_2$N); 3.19 (1H, d, J=4.5 Hz, CH-bridgehead); 3.39 (1H, m, CH of CH$_2$N); 3.45 (1H, dd, J=2.1 and 3.7 Hz, CH of CH$_2$N); 3.96 (1H, dd, J=2.8 and 13.7 Hz, CH of CH$_2$N); 5.26 (1H, m, CH(Me)$_2$); 8.06 (1H, s, pyrazine-H); 8.38 (1H, s, pyrazine-H).

4.
endo-3-[2-(6-Isopropoxypyrazin)yl]-1-azabicyclo[2.2.1]heptane. Hydrochloride endo-3-[2-(6-Isopropoxypyrazin)yl]-3-chloro-1-azabicyclo[2.2.1]heptane (0.5 g, 1.9 mmol) was hydrogenated over 10% Pd/C (0.2 g) as described for Example 8. The crude product was chromatographed through alumina using dichloromethane/methanol (99.5:0.5) as eluant to give the title-endopyrazine as the more polar of two separated components (0.35 g). The hydrochloride salt was prepared, m.p. 132°-135° C. (isopropylalcohol/ethyl acetate); (Found: C, 54.04; H, 7.44; N, 14.46. $C_{13}H_{19}N_3O.1.5HCl$ requires C, 54.23; H, 7.18; N, 14.59%); δ (360 MHz, $D_2O$) 1.37-1.42 (6H, m, 2×Me); 1.74-1.82 (1H, m, CH of $CH_2$); 1.90-2.09 (1H, m, CH of $CH_2$); 3.29-3.31 (1H, m, C$\underline{H}$-bridgehead); 3.37-3.44 (2H, m, $CH_2N$); 3.48-3.57 (2H, m, $CH_2N$); 3.71-3.87 (2H, m, $CH_2N$); 4.03-4.07 (1H, m, C$\underline{H}$-pyrazine); 5.32-5.42 (1H, m, C$\underline{H}(Me)_2$); 8.05 (1H, s, pyrazine-H); 8.12 (1H, s, pyrazine-H).

EXAMPLE 37 exo-3-[2-(6-Isopropoxypyrazin)yl]-1-azabicyclo[2.2.1]heptane. Hydrochloride

The less polar product isolated from the chromatography of Example 36 part 4 was identified as the title exo-pyrazine (0.10 g). The hydrochloride salt was prepared, m.p. 208°-209° C. (isopropylalcohol/ethyl acetate); (Found: C, 56.39; H, 7.27; N, 14.83. $C_{13}H_{19}N_3O$. 1.2 HCl requires C, 56.36; H, 7.35; N, 15.16%); δ (360 MHz, $D_2O$) 1.38 (3H, d, J=6.1 Hz, Me); 1.39 (3H, d, J=6.1 Hz, Me); 1.96-2.06 (1H, m, CH of $CH_2$); 2.17-2.28 (1H, m, CH of $CH_2$); 3.11 (1H, d, J=4.2 Hz, C$\underline{H}$-bridgehead); 3.21 (1H, d, J=9.1 Hz, CH of $CH_2N$); 3.32-3.44 (1H, m, CH of $CH_2N$); 3.48-3.60 (2H, m, $CH_2N$); 3.63-3.69 (1H, m, CH of $CH_2N$); 3.80 (1H, d, J=9.1 Hz, CH of $CH_2N$); 3.86-3.92 (1H, m, C$\underline{H}$-pyrazine); 5.31-5.38 (1H, m, C$\underline{H}(Me)_2$); 8.04 (1H, s, pyrazine-H); 8.12 (1H, s, pyrazine-H).

EXAMPLE 38

3-[2-(6-Chloropyrazin)yl]-3-carbomethoxy-1-azabicyclo[2.2.2]octane

A solution of lithium diisopropylamide in anhydrous THF was prepared by addition of n-butyllithium (6.66 ml of a 1.6M solution in hexane, 10.7 mmol) to a stirred solution of diisopropylamine (1.08 g, 10.7 mmol) in THF (30 ml), at −35° C. The solution was stirred for 0.5 h and then added dropwise to a solution of 3-carbomethoxy-1-azabicyclo[2.2.2]octane (1.5 g, 8.88 mmol) in THF (50 ml), at −78° C. The solution was stirred for 2 h before adding a solution of 2,6-dichloropyrazine (1.59 g, 10.7 mmol) in THF (15 ml), at −78° C. Stirring for 16 h at room temperature was followed by aqueous workup and extraction into dichloromethane. The crude product was chromatographed through silica-gel eluting with dichloromethan/methanol (92:8) to give the title-ester (1.51 g) as a yellow oil; (Found: M+ =281.0920; $C_{13}H_{16}N_3O_2Cl$ requires M+ =281.09310; δ (360 MHz, $CDCl_3$) 1.41-1.55 (2H, m, $CH_2$); 1.64-1.72 (2H, m, $CH_2$); 2.66-2.71 (1H, m, CH of $CH_2N$); 2.73-2.95 (4H, m, $CH_2N$, CH of $CH_2N$ and C$\underline{H}$-bridgehead); 3.64 (1H, dd, J=2.2 and 14.4 Hz, CH of $CH_2N$); 3.67 (3H, s, $CO_2Me$); 3.98 (1H, dd, J=2.2 and 14.4 Hz, CH of $CH_2N$); 8.47 (1H, s, pyrazine-H); 8.57 (1H, s, pyrazine-H).

EXAMPLE 39 exo-3-[2-(3,6-Dimethylpyrazin)yl]-1-azabicyclo[2.2.1]heptan-3-ol 1. 2-Iodo-3,6-dimethylpyrazine 2-Iodo-3,6-dimethylpyrazine was prepared from 2-chloro-3,6-dimethylpyrazine (Aldrich) by the procedure of Hirschberg et al, *J. Org. Chem.* (1961) 26, 1907.

2. exo-3-[2-(3,6-Dimethylpyrazin)yl]-1-azabicyclo[2.2.1]heptan-3-ol

The title-compound was prepared from 1-azabicyclo[2.2.1]heptan-3-one (2.2 g, 19.82 mmol) and 2-iodo-3,6-dimethylpyrazine (4.64 g, 19.82 mmol) using the procedure described in Example 1. Chromatography through alumina using dichloromethane/methanol (96:4) gave the pure product (1.86 g), m.p. 184°-186° C. (ethyl acetate); (Found: C, 65.43; H, 7.83; N, 18.81. $C_{12}H_{17}N_3O$ requires C, 65.73; H, 7.81; N, 19.16%); δ (360 MHz, $CDCl_3$) 1.50-1.59 (1H, m, CH of $CH_2$); 2.04 (1H br s, OH); 2.14-2.24 (1H, m, CH of $CH_2$); 3.36 (1H, dd, J=3.5 and 9.7 Hz, CH of $CH_2N$); 2.43 (3H, s, Me); 2.49 (1H, d, J=9.7 Hz, CH of $CH_2N$); 2.56-2.61 (1H, m, CH of $CH_2N$); 2.58 (3H, s, Me); 2.65-2.71 (1H, m, CH of $CH_2N$); 2.80-2.89 (1H, m, CH of $CH_2N$); 3.27 (1H, dd, J=1.9 and 12.6 Hz, CH of $CH_2N$); 3.42 (1H, d, J=4.2 Hz, C$\underline{H}$-bridgehead); 8.17 (1H, s, pyrazine-H).

EXAMPLE 40 endo-3-[2-(3,6-Dimethylpyrazin)yl]-1-azabicyclo[2.2.1]heptane. Hydrogen Oxalate 1. endo-3-[2-(3,6-Dimethylpyrazin)yl]-3-chloro-1-azabicyclo[2.2.1]heptane The title-chloride was prepared from exo-3-[2-(3,6-dimethylpyrazin)yl]-1-azabicyclo[2.2.1]heptan-3-ol (1 g, 4.57 mmol) using the procedure described for Example 8. The product (0.6 g) was obtained as a yellow oil after chromatography through alumina using ethyl acetate as eluant, m/e 237 (M+); (Found: M+ =237.1038. $C_{12}H_{16}N_3Cl$ requires M+ =237.10328; δ (360 MHz, $CDCl_3$) 0.87-0.95 (1H, m, CH of $CH_2$); 1.62-1.71 (1H, m, CH of $CH_2$); 2.30-2.37 (1H, m, CH of $CH_2N$); 2.50 (3H, s, Me); 2.67 (1H, dd, J=2.7 and 9.9 Hz, CH of $CH_2N$); 2.76 (3H, s, Me); 2.73-2.83 (1H, m, CH of $CH_2N$); 3.40 (1H, d, J=9.9 Hz, CH of $CH_2N$); 3.47 (1H, d, J=4.7 Hz, C$\underline{H}$-bridgehead); 3.48 (1H, d J=12 Hz, CH of $CH_2N$); 4.36-4.46 (1H, m, CH of $CH_2N$); 8.26 (1H, s, pyrazine-H).

2. endo-3-[2-(3,6-Dimethylpyrazin)yl]-1-azabicyclo[2.2.1]heptane. Hydrogen Oxalate The preceding chloride (0.6 g, 2.53 mmol) was hydrogenated over 10% pd on C (0.32 g) as described for previous examples. The crude product was chromatographed on alumina using dichloromethane/methanol (99.5:0.5) as eluant to give the title-endopyrazine as the more polar of two separated components (0.4 g). The hydrogen oxalate salt was prepared, m.p. 199°-200° C. (isopropyl alcohol), (Found: C, 57.26; H, 6.49; N, 14.21. $C_{12}H_{17}N_3.(CO_2H)_2$ requires C, 57.33; H, 6.53; N, 14.33%); m/e 203 (M+); δ (360 MHz, $D_2O$) 1.42-1.54 (1H, m, CH of $CH_2$); 1.78-1.90 (1H, m, CH of $CH_2$); 2.53 (3H, s, Me); 2.56 (3H, s, Me); 3.36-3.63 (6H, m, 2 of $CH_2N$, CH of $CH_2N$ and C$\underline{H}$-bridgehead); 4.10-4.22 (2H, m, CH of $CH_2N$ and C$\underline{H}$-pyrazine); 8.23 (1H, s, pyrazine-H).

EXAMPLE 41 exo-3-[2-(3,6-Dimethylpyrazin)yl]-1-azabicyclo[2.2.1-]pyrazine. Hydrogen Oxalate The less polar product isolated from the chromatography of Example 40 part 2 was identified as the title exo-pyrazine (50mg). The hydrogen oxalate salt was prepared, m.p. 183°–185° C. (isopropylalcohol), (Found: C, 56.87; H, 6.57; N, 14.06. $C_{12}H_{17}N_3$.$(CO_2H)_2 0.1 H_2O$ requires C, 56.98; H, 6.56; N, 14.24%): m/e 203 (M+); δ (360 MHz, $D_2O$) 1.98–2.08 (1H, m, CH of $CH_2$); 2.18–2.28 (1H, m, CH of $CH_2$); 2.50 (3H, s, Me); 2.54 (3H, s, Me); 3.07 (1H, d, J=4.3 Hz, CH-bridgehead); 3.11 (1H, d, J=9.1 Hz, CH of $CH_2N$); 3.34–3.42 (1H, m, CH of $CH_2N$); 3.46–3.60 (3H, m, $CH_2N$ and CH of $CH_2N$); 3.67 (1H, dd, J=5.5 and 8.2 Hz, CH of $CH_2N$); 4.15–4.20 (1H, m, CH-pyrazine); 8.21 (1H, s, pyrazine-H).

EXAMPLE 42 endo-3-[2-(6-Allyloxypyrazin)yl]-1-azabicyclo[2.2.1-]heptane. Dihydrochloride

1. 2-Iodo-6-allyloxypyrazine

This was prepared from 2,6-diiodopyrazine (5.5 g, 16.6 mmol) and allyl alcohol by the procedure described for Example 31 part 1. Chromatography through silica gel using dichloromethane as eluant gave the pure product (2 g), δ (250 MHz, $CDCl_3$) 4.83–4.86 (2H, m, $CH_2O$); 5.29–5.35 (1H, m, cis-vinyl-H); 5.39–5.48 (1H, m, trans-vinyl-H); 5.98–6.13 (1H, m, vinyl-H); 8.16 (1H, s, pyrazine-H); 8.40 (1H, s, pyrazine-H).

2. exo-3-[2-(6-Allyloxypyrazin)yl]-1-azabicyclo[2.2.1]heptan-3-ol

The title-alcohol was prepared from 1-azabicyclo[2.2.1]heptan-3-one (0.85 g, 7.66 mmol) and 2-iodo-6-allyloxypyrazine (2 g, 7.63 mmol) by the procedure described for Example 1. The crude product was chromatographed through alumina using dichloromethane/methanol (96:4) as eluant to give the desired alcohol (0.81 g) as a pale yellow oil (Found: M+=247.1320.$C_{13}H_{17}N_3O_2$ requires M+=247.1321); δ (360 MHz, $CDCl_3$) 1.49–1.57 (1H, m, CH of $CH_2$); 2.30–2.36 (1H, m, CH of $CH_2$); 2.47 (1H, dd, J=3.6 and 10 Hz, CH of $CH_2N$); 2.57 (1H, dd, J=3.6 and 13 Hz, CH of $CH_2N$); 2.72 (1H, d, J=3.9 Hz, CH-bridgehead); 2.72–2.80 (1H, m, CH of $CH_2N$); 2.92–3.00 (1H, m, CH of $CH_2N$); 3.09 (1H, d, J=10 Hz, CH of $CH_2N$); 3.39 (1H, dd, J=1.8 and 13 Hz, CH of $CH_2N$); 4.83–4.86 (2H, m, $CH_2O$); 5.28–5.31 (1H, m, cis-vinyl-H); 5.38–5.44 (1H, m, trans-vinyl-H); 6.00–6.10 (1H, m, vinyl-H); 8.15 (1H, s, pyrazine-H); 8.38 (1H, s, pyrazine-H).

3. endo-3-[2-(6-Allyloxypyrazin)yl]-3-chloro-1-azabicyclo[2.2.1]heptane

The title-chloride was prepared from exo-3-[2-(6-allyloxypyrazin)yl]-1-azabicyclo[2.2.1]heptan-3-ol (0.81 g. 3.28 mmol) by the procedure described for Example 8. The crude product was chromatographed through alumina using ethyl acetate as eluant to give the desired chloride (0.26 g) as a yellow oil, (Found: M+=265.0975. $C_{13}H_{16}N_3OCl$ requires M+=265.0982); δ (360 MHz, $CDCl_3$) 0.94–1.02 (1H, m, CH of $CH_2$); 1.57–1.66 (1H, m, CH of $CH_2$); 2.37–2.45 (1H, m, CH of $CH_2N$); 2.67 (1H, dd, J=2.5 and 9.7 Hz, CH of $CH_2N$); 2.76–2.86 (1H, m, CH of $CH_2N$); 3.19 (1H, d, J=4.5, CH-bridgehead); 3.38–3.41 (1H, m, CH of $CH_2N$); 3.45 (1H, dd, J=2.1 and 13.7 Hz, CH H of $CH_2N$); 3.97 (1H, dd, J=2.5 and 13.7 Hz, CH of $CH_2N$); 4.86–4.88 (2H. m $CH_2$—O); 5.28–5.32 (1H, m, cis-vinyl-H); 5.39–5.45 (1H. m, trans-vinyl-H); 6.01–6.11 (1H, m, vinyl-H); 8.15 (1H, s, pyrazine-H); 8.43 (1H, s, pyrazine-H).

4. endo-3-[2-(6-Allyloxypyrazin)yl]-1-azabicyclo[2.2.1]heptane. Dihydrochloride Tributyltin hydride (0.4 ml, 1.37 mmol) was added to a stirred solution of the preceding chloride (0.26 g. 0.98 mmol), in anhydrous THF (10 ml), followed by a catalytic amount of AIBN. The mixture was refluxed for 1.5 h before cooling to room temperature and adding a second portion of tributyltin hydride (0.4 ml, 1.37 mmol) and AIBN. Refluxing for 2 h was followed by cooling to room temperature and adding dichloromethane (50 ml) and 2N hydrochloric acid (10 ml) and stirring for 0.1 h. The aqueous was washed with dichloromethane (20 ml) and the combined dichloromethane washed with 2N hydrochloric acid (2×25 ml). The combined aqueous was basified with potassium carbonate and extracted with dichloromethane (5×50 ml). The combined extracts were dried ($Na_2SO_4$) and the residue remaining, after removal of solvent, chromatographed through alumina using dichloromethane/methanol (98:2) as eluant to give the title-product. The dihydrochloride salt was prepared, m.p. 147°–149° C. (isopropyl alcohol/ether), (Found: C, 50.85; H, 6.25; N, 13.56. $Cl_3H_{17}N_3O.1$ HCl, 0.1 $H_2O$ requires C. 51.02; H, 6.32; N, 13.73%); m/e 231 (M+); δ (360 MHz, $D_2O$) 1.68–1.78 (1H, m, CH of $CH_2$); 1.85–1.97 (1H, m, CH of $CH_2$) 3.28–3.30 (1H, m, CH-bridgehead); 3.36–3.56 (4H, m, 2×$CH_2N$); 3.70–3.77 (1H, m, CH of $CH_2N$); 3.82–3.87 (1H, m, CH of $CH_2N$); 4.02–4.07 (1H, m, CH-Pyrazine): 4.97–5.02 (2H, m, $CH_2O$); 5.30–5.43 (2H, m, $CH_2$ of vinyl); 6.07–6.18 (1H, m, CH-vinyl); 8.17 (2H, s, pyrazine-H's).

EXAMPLE 43 exo-3-[2-(6-Allyloxypyrazin)yl]-1-azabicyclo[2.2.1]heptane. Hydrochloride

Sodium metal (50 mg, 2.2 mmol) was added to allyl alcohol (3 ml) at room temperature and once dissolved, a solution of endo-3-[2-(6-allyloxypyrazin)yl]-1-azabicyclo[2.2.1]heptane (0.15 g. 0.64 mmol) in allyl alcohol (1ml) was added, with stirring, and the mixture refluxed for 2 h. The solution was cooled to 60° C. and the solvent removed by distillation under vacuum. The residue was taken up into dichloromethane and chromatographed through alumina using dichloromethane/methanol (99.5:0.5) as eluant to give the title-Pyrazine (0.10 g) as a clear oil.

The hydrochloride salt was prepared, m.p. 186°–189° C. alcohol/ether); (Found: C, 57.64; H, 7.76; N, 15.41. $C_{13}H_{17}N_3 0.1$ HCl.0.2$H_2O$ requires C, 57.54; H, 6.83; N. 15.48%); m/e 231 (M+); δ (360 MHz, $D_2O$) 1.96–2.40 (1H, m, CH of $CH_2$); 2.16–2.26 (1H, m, CH of $CH_2$) 3.10 (1H, d, J=4 Hz, CH-bridgehead); 3.19 (1H, d. J=9.2 Hz, CH of $CH_2N$); 3.33–3.44 (1H, m, CH of $CH_2N$) 3.50–3.60 (2H, m, 2× CH of $CH_2N$); 3.61–3.68 (1H, m, CH of $CH_2N$); 3.80 (1H, d, J=9.2 Hz, CH of $CH_2N$); 3.87–3.94 (1H, m, CH-yrazine); 4.94–4.97 (2H, m, CH$_2$—O): 5.32-5.45 (2H, m, vinyl-CH$_2$); 6.09-6.17 (1H, m, vinyl-CH); 8.14 (1H, s, Pyrazine-H); 8.15 (1H, s, pyrazine-H).

EXAMPLE 44 exo and endo-3-[2-(3-Ethylpyrzin)yl]-azabicyclo[2.2.1]heptane. Dihydrogen Oxalate

1. 2-Hydroxy-3-ethyloyrazine

The title -compound was prepared from α-aminobutyramide hydrobromide and glyoxal as described by Karmas and Spoerri, *J. Am. Chem. Soc.*, 1952, 74, 1580, m.p. 95°-97° C. (Lit. 96°-97° C.).

2. 2-Iodo-3-ethylpyrazine

This was prepared from 2-hydroxy-3-ethyl-pyrazine by the procedure of Hirschberg and Spoerri, *J. Org. Chem.*, 1961, 1907.

3 exo-3-[2-(3-Ethylpyrazin)yl]-1-azabicyclo[2.2.1]heptan-3-ol

The title -compound was prepared from 1-azabicyclo[2.2.1]heptan-3-one (2.0 g, 18.0 mmol) and 2 iodo-3-ethylpyrazine (4.2 g, 18.0 mmol) using the procedure described for Example 1. The crude product was purified by chromatography through alumina using dichloromethane/methanol (96:4) as eluant. The product (0.75 g) Was obtained as a crystalline solid, m.p. 165°-167° C., m/e 219 (M$^-$) δ (360 MHz, CDCl$_3$) 1.30 (3H, t, J=7.4 Hz, Me); 1.50-1.61 (1H, m, CH of CH$_2$); 2.15-2.25 (1H, m, CH of CH$_2$); 2.38 (1H, dd, J=3.4 and 10 Hz, CH of CH$_2$N); 2.49 (1H d, J=10 Hz, CH of CH$_2$N); 2.63 (1H, dd, J=3.4 and 12.6 Hz, CH of CH$_2$N); 2.62-2.72 (1H, m, CH of CH$_2$N); 2.80-3.00 (3H, m, CH of CH$_2$N and CH$_2$); 3.22 (1H, d, J=12.6 Hz, CH of CH N); 3.38 (1H, d, 4.2 Hz, CH-bridgehead); 8.18 (1H, d, J=2.5 Hz, pyrazine-H); 8.38 (1H, d, J=2.5 Hz, pyrazine-H).

4. endo-3-[2-(3-Ethylpyrazin)yl]-3-chloro-1-azabicyclo[2.2.1]heptane

This was prepared from the Preceding alcohol (0.7 g, 3.2 mmol) by the procedure described for Example 8. The product (0.24 g) was obtained as a low melting solid after chromatography through alumina using ethyl acetate as eluant, m.p. 63°-65° C., (Found: M$^-$=237.1035; C$_{12}$H$_{16}$N$_3$Cl requires M$^+$=237.1033; 0.90 (1H, br s, CH of CH$_2$); 1.38 (3H, t, J=7.3 Hz, Me); 1.62-1.72 (1H, m, CH of CH$_2$); 2.31-2.38 (1H, m, CH of CH$_2$N); 2.66 (1H dd, J=2.5 and 9.6 Hz, CH of CH$_2$N); 2.73-2.81 (1H, m, CH of CH$_2$N) 3.05-3.16 (2H, m, CH$_2$); 3.40-3.45 (2H, m, CH of CH$_2$N and CH-bridgehead); 3.51 (1H, d. J=13.8 Hz, CH of CH N); 4.30 (1H, br s. CH of CH$_2$N); 8.30 (1H, d, J=2.4 Hz. Pyrazine-H); 8.46 (1H, d, J=2.4 Hz, pyrazine-H).

5. exo-and endo-3-[2-(3-Ethylpyrazin)yl]-1-azabicyclo[2.2.1]heptane. Dihydrogen Oxalate The preceding chloride (0.45 g, 1.68 mmol) was hydrogenated in the usual way to give after chromatography through alumina with dichloromethane/methanol (99.5:0.5) as eluant, the title-endopyrazine (0.39 g). The dihydrogenoxalate salt was prepared, m.p. 105°-107° C. (isopropyl alcohol/ethyl acetate): (Found: C. 50.20: H, 5.72; N, 11.18. C$_{12}$H$_{17}$N$_3$. 2((CO$_2$H)$_2$ requires C, 50.13; H, 5.52; N, 10.96%); m/e 203 M$^-$); & (360 MHz, D$_2$O) 1.29 (3H, t, J=10.9 Hz, Me); 1.45-1.58 (1H, m, CH of CH$_2$); 1.80-1.97 (1H, m, CH of CH$_2$); 2.86-3.12 (2H, m, CH$_2$Me); 3.33-3.65 (5H, m, 2 of CH$_2$N and CH-bridgehead); 3.71 (1H, d, J=16.5 Hz, CH of CH$_2$N); 4.00-4.08 (1H, m, CH of CH$_2$N); 4.26-4.37 (1H, m, CH-pyrazine); 8.45 (1H, d, J=4.0 Hz, pyrazine-H); 8.63 (1H, d, J=4.0 Hz, pyrazine-H). The less polar component (0.05 g) was identified as the exo-diastereoisomer.

EXAMPLE 45 endo-3-[2-(3-Methylpyrazin)yl]-1-azabicyclo [2.2.11 heptane. Dihydrochloride

1. exo-3-[2-(3-Methylpyrazin)yl]-1-azabicyclo[2.2.1]heptan-3-ol

This was prepared from 1-azabicyclo[2.2.1]heptan-3-one (2.48 g. 22.0 mmol) and 2-iodo-3-methyl-pyrazine (3.78 g. 17.2 mmol) using the procedure described for Example 1. Chromatography through alumina eluting with dichloromethane/methanol (98:2) gave the pure product (1.61 g); (Found: M$^+$=205.1206. C$_{11}$H$_{15}$N$_3$O requires M$^+$=205.12151); δ (360 MHz, CDCl$_3$) 1.51-1.59 (1H, m, CH of CH$_2$); 2.15-2.24 (1H, m, CH of CH$_2$); 2.37 (1H, dd, J=3.4 and 10 Hz, CH of CH$_2$N); 2.48 (1H, d, J=10 Hz, CH of CH$_2$N); 2.61 (1H, dd, J=3.4 and 12.6 Hz, CH of CH$_2$N); 2.64 (3H, s, Me); 2.64-2.87 (2H, m, CH$_2$N); 3.21 (1H, dd, J=1.8 and 12.6 Hz, CH of CH$_2$N); 3.39 (1H, d, J=4.2 Hz, CH-bridgehead); 8.19 (1H, d, J=2.5 Hz, pyrazine-H); 8.30 (1H, d, J=2.5 Hz. pyrazine-H).

2 endo-3-[2-(3-Methylpyrazin)yl]-3-chloro-1azabicyclo-[2.2.1]heptane

This was prepared from the preceding alcohol (1.5 g, 7.3 mmol) using the procedure described for Example 8. The product (0.37 g) was isolated as a yellow oil; (Found M$^+$=223.0868.C$_{11}$H$_{14}$N$_3$Cl requires M$^+$=223.08763); δ (360 MHz, CDCl$_3$) 0.85-0.98 (1H, m, CH of CH$_2$); 1.62-1.78 (1H, m, CH of CH$_2$); 2.28-2.40 (1H, m, CH of CH$_2$N); 2.67 (1H, dd, J=2.7 and 9.8 Hz, CH of CH$_2$N); 2.60-2.81 (1H. m, CH of CH$_2$N); 2.82 (3H, s, Me); 3.40 (1H d, J=9.8 Hz, CH of CH$_2$N); 3.48 (1H, d, J=4.8 Hz. CH-bridgehead); 3.50 (1H, d, J=14.7 Hz, CH of CH$_2$N); 4.25-4.36 (1H, m, CH of CH$_2$N); 8.32 (1H. d, J=2.4 Hz, pyrazine-H); 8.40 (1H, d, J=2.4 Hz, pyrazine-H).

3. endo-3-[2-(3-Methylpyrazin)yl]-1-azabicyclo[2.2.1]heptane. Dihydrochloride The preceding chloride (0.37 g 1.7 mmol) was hydrogenated using the general procedure to give, after chromatography through alumina using dichloromethane/methanol (99:1) as eluant. The title-product. The dihydrochloride salt was prepared, m.p. 166°-168° C. (isopropylalcohol/ether); (Found: C, 47.26; H. 6.77: N, 15.05. C$_{11}$H$_{15}$N$_3$.2 HCl.H$_2$O requires C, 47.15; H, 6.84; N, 15.00%); m/e 189 M$^+$); δ (360 MHz, D$_2$O) 1.43-1.52 (1H, m, CH of CH$_2$); 1.82-1.96 (1H, m, CH of CH$_2$); 2.71 (3H, s, Me); 3.40-3.50 (4H, m, CH of CH$_2$N, CH$_2$N and CH-bridgehead); 3.61 (1H, d, J=8.3 Hz, CH of CH$_2$N); 3.68-3.74 (1H, m, CH of CH$_2$N); 4.02-4.08 (1H, m, CH of CH$_2$N); 4.26-4.32 (1H, m, CH-pyrazine); 8.45 (1H, d, J=3 Hz, pyrazine-H); 8.72 (1H, d, J=3 Hz, pyrazine-H).

EXAMPLE 46

3-[2-(6-Chloropyrazin)yl]-1-azabicyclo[2.2.2]octane. Hydrochloride

A solution of 3-[2-(6-chloropyrazin)yl]-3-carbomethoxy-1-azabicyclo[2.2.2]octane (1.0 g, 3.6 mmol) in concentrated (35%) hydrochloric acid (40 ml) was heated at 125° C. for 4 h. The solution was cooled to 10° C., dichloromethane (100 ml) added, and the aqueous basified to pH 10 with potassium carbonate, with stirring. The aqueous was separated and extracted with several portions of dichloromethane (4×50 ml). The residue remaining, after drying ($Na_2SO_4$) and removal of solvent, was chromatographed through alumina, eluting with dichloromethane/methanol (96:4) to give the title-chloropyrazine (0.25 g). The hydrochloride salt was prepared, m.p. 149°14 151° C. (isopropyl alcohol/ether); (Found: C, 48.00; H, 5.79; N, 15.08. $C_{11}H_{14}N_3Cl.1.4$ HCl requires C, 48.09; H, 5.65; N 15.29%); m/e 223 M+); δ (360 MHz, $D_2O$) 1.73–1.90 (2H, m. $CH_2$) 2.08–2.28 (2H, m, $CH_2$); 2.44–2.47 (1H, m, bridgehead-H); 3.29–3.38 (1H, m, CH of $CH_2N$); 3.42–3.56 (3H, m, $CH_2N$ and CH of $CH_2N$); 3.62–3.69 (1H, m, CH of $CH_2N$); 3.77–3.82 (1H, m, CH of $CH_2N$); 4.01 (1H, dd, J=6.3 and 12.7 Hz, CH-pyrazine); 8.58 (1H, s, pyrazine-H); 8.59 (1H, s, pyrazine-H).

EXAMPLE 47 exo-3-[2-(3-Methylpyrazin)yl]-1-azabicyclo[2.2.1]heptane. Hydrochloride

Sodium methoxide (0.25 g. 6.25 mmol) was added to a solution of endo-3-[2-(3-methylpyrazin)yl]-1-azabicyclo[2.2.1]heptane (0.15 g. 0.8 mmol) and the solution refluxed for 16 h. The solvent was removed under vacuum. The residue taken up into dichloromethane and chromatographed through alumina eluting with dichloromethane/methanol (99:1) to give the less polar exo-diastereoisomer (70 mg). The hydrochloride salt was prepared, m.p. 214°–216° C. (ethyl acetate/isopropyl alcohol/ether); (Found: C, 55.16; H, 7.00; N, 17.54. $C_{11}H_{15}N_3.1.4$ HCl requires C, 54.98; H, 6.88; N, 17.49%) m/e 189 (M+); δ (360 MHz, $D_2O$) 2.02–2.12 (1H, m, CH of $CH_2N$); 2.20–2.30 (1H, m, CH of $CH_2N$); 2.61 (3H, s, Me); 3.13–3.17 (2H, m, CH of $CH_2N$ and CH-bridgehead; 3.36–3.44 (1H, m, CH of $CH_2N$); 3.49–3.66 (3H, m, $CH_2N$ and CH of $CH_2N$); 3.74 (1H dd, J=5.4 and 8.1 Hz, CH of $CH_2N$); 4.06–4.11 (1H, m, CH-pyrazine); 8.36 (1H, d, J=2.8 Hz, pyrazine-H); 8.47 (1H, d, J=2.8 Hz, pyrazine-H).

EXAMPLE 48 exo and endo-3-2-(6-Chloropyrazin)yl]-1azabicyclo[2.2.1]heptane. Hydrogen Oxalate

1.

exo-3-[2-(6-Chloropyrazin)yl-3-carbomethoxy-1-azabicyclo[2.2.1]heptane

A solution of lithium diisopropylamide in THF (20 ml) was prepared by addition of n-butyllithium (14.5 ml of a 1.6M solution in hexane. 23.2 mmol) to a solution of diisopropylamine (2.35 g, 23.5 mmol) in THF (20 ml), at −50° C. The solution was stirred for 0.5 h and then added, at −78° C. to a solution of exo-3and carbomethoxy-1-azabicyclo[2.2.11 heptane (3 g, 19.35 mmol, prepared as described in EP 0239309) in THF (50 ml), at −78° C. The solution was stirred for 2 h before adding a solution of 2,6-dichloropyrazine (3.5 g, 23.5 mmol) in THF (10 ml). The reaction mixture was warmed to room temperature and stirred for 16 h. Water (40 ml) and dichloromethane (150 ml) were added and stirred for 0.1 h before separating the aqueous and further extracting with dichloromethane (3×100 ml). The combined extracts were dried ($Na_2SO_4$), evaporated, and the residue chromatographed through silica-gel, eluting with dichloromethane/methanol (92:8) to give the title pyrazine (1.8 g); (Found: M+ =267.0763. $C_{12}H_{14}N_3O_2Cl$ requires M+ =267.07745); δ (360 MHz, $CDCl_3$) 1.28–1.37 (1H, m, CH of $CH_2$); 1.69–1.78 (1H m, CH of $CH_2$); 2.52–2.59 (2H, m, $CH_2N$); 2.65–2.72 (1H, m, CH of $CH_2N$); 2.89–2.97 (1H, m, CH of $CH_2N$); 3.19 (1H, dd, J=2.2 and 12.8 Hz, CH of $CH_2N$); 3.50 (1H, d, J=4.2 Hz, CH-bridgehead): 3.67 (3H, s $CO_2Me$): 3.70 (1H, dd, $\overline{J}$=2.67 and 12.8 Hz, CH of $CH_2N$); 8.47 (1H, s, pyrazine-H); 8.49 (1H, s, pyrazine-H).

2. exo and endo-3-2-(6-Chloropyrazin)yl]-1-azabicyclo[2.2.1]heptane. Hydrogen Oxalate A solution of the preceding ester (1.8 g. 6.73 mmol) in concentrated hydrochloric acid (30 ml) was refluxed for 4 h. The solution was cooled to 10° C., dichloromethane (100 ml) added and the aqueous basified to pH 10 with potassium carbonate. The aqueous was separated and further extracted with dichloromethane (5×100 ml). The combined extracts were dried ($Na_2SO_4$), the solvent removed under vacuum and the residue chromatographed through alumina eluting with dichloromethane/methanol (98:2) to give the title-product (0.6 g). The hydrogen oxalate salt was prepared m.p. 159°–161° C. (isopropyl alcohol); (Found: C, 48.07; H. 4.74; N, 13.92. $C_{10}H_{12}N_3Cl.(CO_2H)_2$ requires C, 48.09; H, 4.71; N, 14.02%); m/e 209 (M ); δ (360 MHz, 30 $CDCl_3$, free base) 1.18–1.25 (1H, m. CH of $CH_2$); 1.38–1.47 (1H, m, CH of $CH_2$) 2.59–2.62 (1H, m, CH of $CH_2N$); 2.62–2.79 (2H, m, CH of $CH_2N$); 2.85–3.10 (3H, m, CH-bridgehead, and $CH_2N$); 3.16–3.23 (1H m, CH of $CH_2N$); 3.44–3.49 (1H, m, CH-pyrazine); 8.38 (1H, s, pyrazine-H); 8.42 (1H s, pyrazine-H). The less polar isomer from the chromatography was identified as the exo-diastereoisomer (50 mg): (Found: M+ =209.0700 $C_{10}H_{12}N_3Cl$ requires M+ =209.07198).

EXAMPLE 49

6-[2-(6-Chloropyrazin)yl]-2-azabicyclo2.2.2]octane. Isomers A and B

2-Carbo-t-butyloxy-6-carbomethoxy-2-azabicyclo[2.2.2]octane

Di-t-butyldicarbonate (21.8 g, 0.10 mmol) in dry dichloromethane (50 ml) was added dropwise to a stirred, cooled (0° C.) solution of 6-carbomethoxy-2azabicyclo[2.2.2]octane (18.2 g. 0.09 mmol, mixture of endo and exo isomers, prepared as described in Example 21a, EP 0239309) in dry dichloromethane (100 ml). The resulting solution was stirred at room temperature for 4 h. water (100 ml) added and the mixture stirred for 0.25 h. The organic layer was separated and washed with 0.5M hydrochloric acid (100 ml), water (100 ml), saturated sodium hydrogen carbonate solution (100 ml), water (100 ml) then dried ($Na_2SO_4$) and evaporated. The residue was purified by column chromatography on silica by elution with ethyl acetate/petroleum ether (60–80), (2.5:97.5) to give Isomer A as a colourless oil which crystallised on standing (12.0 g), m.p. 44°-45° C., Rf=0.35 in ethyl acetate/petroleum ether (60-80) (50:50) on silica: (Found: C, 62.59; H, 8.55; N, 5.10. $C_{14}H_{23}NO_4$ requires C, 62.43; H 8.61; N, 5.20%); m/e 269 M+); δ (360 MHz, $CDCl_3$) 1.47 (9H, s, 3 of Me); 1.55-2.20 (7H, m, 3 of $CH_2$ and CH-bridgehead); 2.86-3.00 (1H, m, C$\underline{H}$—$CO_2Me$); 3.30 (2$\overline{H}$, br s, $CH_2N$); 3.69 and 3.72 (total $\overline{3H}$, each br s, $CO_2Me$, rotamers); 4.21 and 4.38 (total 1H, each br s, C$\underline{H}$N-bridgehead, rotamers). Mixed fractions were collected (1:1 mixture, 4.80 g), followed by Isomer B as a colourless oil (6.80 g). Rf=0.32 in ethyl acetate/petroleum ether (60-80) (50:50) on silica; m/e 269 M+); δ (360 MHz, $CDCl_3$) 1.42 and 1.43 (total 9H, each s, 3 of Me, rotamers); 1.52-2.20 (7H, m, 3 of $CH_2$ and CH-bridgehead): 2.63-2.73 (1H, m, C$\underline{H}$—$CO_2Me$); 3.19-3.25 (1H, m, CH of $CH_2N$); 3.36-3.4$\overline{2}$ (1H, m, CH of $CH_2N$); 3.66 and 3.69 (total 3H, each s, $CO_2Me$, rotamers): 4.27-4.30 and 4.36-4.38 (each total 1H, each m, C$\underline{H}$-N-bridgehead, rotamers).

2.
2-Carbo-t-butyloxy-6-[2-(6-chloropyrazin)yl]-6-carbomethoxy-2-azabicyclo[2.2.2]octane. Isomers A and B A solution of lithium diisopropylamide was prepared by addition of n-butyllithium (1.5 ml of a 1.6M solution in hexane. 2.4 mmol) to a solution of diisopropylamine (0.33 ml, 2.4 mmol) in THF (20 ml), at −40° C.. The solution was stirred for 0.5 h before adding a solution of a mixture of the preceding esters (0.54 g, 2.0 mmol) in THF (10 ml), at −60° C., and stirring for 0.5 h. A solution of 2,6-dichloropyrazine (0.36 g, 2.4 mmol) in THF (10 ml) was added to the reaction mixture and allowed to warm to room temperature overnight. Water (10 ml) and dichloromethane (100 ml) were added and stirred for 0.1 h. The aqueous was separated and extracted with further portions of dichloromethane (3×50 ml). The combined extracts were dried ($Na_2SO_4$) and evaporated and the residue chromatographed through silica-gel eluting with ethyl acetate/petroleum ether (60-80) (50:50) to give 2-isomers. The less polar isomer (250 mg) was obtained as a low melting solid, (Found: M+=381.1447. $C_{18}H_{24}N_3O_4Cl$ requires M+=381.14553): δ (360 MHz, $CDCl_3$) 1.33 and 1.39 (total 9H, each s, 3 of Me, rotamers); 1.60-2.20 (7H, m, 3 of $CH_2$ and CH-bridgehead); 3.10-3.30 (2H, m, $CH_2N$); 3.68 and 3.$\overline{70}$ (total 3H, each s, $CO_2Me$, rotamers): 4.74-4.77 and 4.90-4.93 (total 1H, each m, C$\underline{H}$-N-bridgehead, rotamers); 8.45 and 8.46 (total 1H, ea$\overline{ch}$ s, pyrazine-H, rotamers); 8.77 and 8.84 (total 1H, each s, pyrazine-H, rotamers). The more Polar isomer (350 mg) was obtained as a low melting solid; (Found: M+=381.1475. $C_{18}H_{24}N_3O_4Cl$ requires M+=381.14553); δ (360 MHz, $CDCl_3$) 1.46 and 1.50 (total 9H, each s, 3 of Me, rotamers); 1.52-2.30 (6H, m, 3 of $CH_2$); 2.97-3.03 (1H, m, C$\underline{H}$-bridgehead); 3.26-3.44 (2H, m, $CH_2N$); 3.60 and 3.64 (total 3H, each s, $CO_2Me$, rotamers); 4.91-4.93 and 5.07-5.09 (total 1H, each m, C$\underline{H}$N-bridgehead, rotamers); 8.47 and 8.48 (total 1H, each s, pyrazine-H, rotamers); 8.60 and 8.64 (total 1H, each s, pyrazine-H, rotamers).

3. 6-[2-(6-Chloropyrazin)yl]-2-azabicyclo[2.2.2]octane. Isomers A and B

A solution of the preceding ester (0.5 g, 1.3 mmol, less polar isomer) in concentrated hydrochloric acid (20 ml) was refluxed for 4H. The solution was cooled to room temperature, basified with potassium carbonate and extracted into dichloromethane (5×70 ml). The combined extracts were dried ($Na_2SO_4$), evaporated, and the residue chromatographed through alumina, eluting with dichloromethane/methanol (96:4) to give the title-pyrazine, Isomer A, (0.12 g); (Found: M+=233.0873. $C_{11}H_{14}N_3Cl$ requires M+=223.08763); δ (360 MHz, $CDCl_3$) 1.62-1.73 (1H, m, CH of $CH_2$); 1.78-2.08 (7H, m, 2 of $CH_2$, CH of $CH_2$, CH-bridgehead and NH); 2.89 (1H, br s, CH-bridgehead); 3.00 (1H, d, J=10.75 Hz, CH of $CH_2N$); 3.12-3.18 (2H, m, CH of $CH_2N$ and C$\underline{H}$-pyrazine); 8.43 (1H, s, pyrazine-H); 8.44 (1H, s, pyrazine-H).

Using the procedure described for Isomer A, the more polar ester (Example 49, part 2) was treated with hydrochloric acid to give 6-[2-(6-Chloropyrazin)yl]-2-azabicyclo[2.2.2]octane, Isomer B. (Found: M+=2.23.0872 $C_{11}H_{14}N_3Cl$ requires M+=223.0876); δ (360 HMz, $D_2O$) 1.71-1.94 (4H, m, 2 of $CH_2$); 2.20-2.28 (3H, CH-bridgehead and $CH_2$); 3.36 (2H, brs, $CH_2N$); 3.68-3.73 (1H, m, CH-pyrazine); 3.80-3.82 (1H, m, CH-bridgehead); 8.56 (2H, s, pyrazine-H).

EXAMPLE 50

6-[2-(6-Methoxypyrazin)yl]-2-azabicyclo[2.2.2]octane. Hydrochloride. Isomers A and B Sodium methoxide (0.25 g, 6.25 mmol) was added to a solution of the preceding chloride (0.12 g, 0.54 mmol. Isomer A) in methanol (15 ml) and refluxed for 16 h. The solvent was removed under vacuum, the residue taken up into water (3 ml) and extracted with dichloromethane (5×20 ml). The combined extracts were dried ($Na_2SO_4$), evaporated and the residue chromatographed through alumina eluting with dichloromethane/methanol (97.5:2.5) to give the title-isoquinuclidine (56 mg, Isomer A). The hydrochloride salt was prepared. m.p. 170°-172° C. (isopropyl alcohol/ether): (Found: C. 51.73; H, 6.86: N, 14.79. $C_{12}H_{17}N_3O.1.65$ HCl requires C, 51.58; H, 6.73; N, 15.04%); m/e 219 M+); δ (360 MHz, $D_2O$) 1.80-2.14 (5H, m 2 of $CH_2$ and CH of $CH_2$); 2.14-2.18 (1H, m, C$\underline{H}$ -bridgehead); 2.24-2.33 (1H, m, CH of $CH_2$) 3.30-$\overline{3}$.34 (1H. br d, J=12 Hz, CH of $CH_2N$); 3.45 (1H, dd, J=6.2 and 12.0 Hz, C$\underline{H}$-pyrazine); 3.55 (1H. br d, J=12 Hz, CH of $CH_2N$); 3.74 (1H, br s, C$\underline{H}$N-bridgehead); 4.02 (3H, s, OMe); 8.10 (1H, s, pyrazine-H); 8.17 (1H, s, pyrazine-H).

Using the Procedure described for Isomer A, 6-[2-(6-chloropyrazin)yl]-2-azabicyclo[2.2.2]octane (Isomer B) was treated with sodium methoxide to give 6-[2-(6-methoxypyrazin)yl]-2-azabicyclo[2.2.2]octane, Isomer B.

EXAMPLE 51 endo-3-[2-(3,5-Dimethylpyrazin)yl]-1-azabicyclo[2.2.1]heptane. Dihydrochloride 1. 2-Hydroxy-3,5-dimethylpyrazine The title-compound was prepared from alanine amide hydrochloride and pyruvic aldehyde as described by Karmas and Spoerri, *J. Am. Chem. Soc.,* 1952, 74, 1580 m.p.=149.5°-151° C. (Lit. 146°-147° C.).

2. 2-Iodo-3,5-dimethylpyrazine

This was prepared from 2-hydroxy-3,5-dimethylpyrazine by the Procedure of Hirschberg and Spoerri, *J. Org. Chem.,* 1961, 1907.

3
exo-3-[2-(3,5-Dimethylpyrazin)yl]-1-azabicyclo[2.2.1]heptan-3-ol

The title-compound was prepared from 1-azabicyclo 2.2.1]heptan-3-one (3 g, 27.0 mmol) and 2-iodo-3,5-dimethylpyrazine (6.3 g, 27.0 mmol) using the procedure described for Example 1. The crude product was purified by chromatography through alumina using dichloromethane/methanol (98:2) as eluant. The product (3.1 g) was obtained as a crystalline solid. m.p. 172°–175° C.; (Found: M=219.1372. $C_{12}H_{17}N_3O$ requires $M^+$ =219.1385): δ (250 MHz, $CDCl_3$) 1.45–1.56 (1H, m, CH of $CH_2$): 2.10–2.24 (1H, m, CH of $CH_2$); 2.31 (1H, dd J=3.4 and 9.4 Hz, CH of $CH_2N$); 2.40 (1H, d, J=9.4 Hz, CH of $CH_2N$); 2.47 (3H, s, Me); 2.50–2.69 (3H, m, 2 of CH of $CH_2N$ and OH); 2.57 (3H, s, Me); 2.69–2.84 (1H, m, CH of $CH_2N$); 3.07 (1H, dd, J=1.5 and 2.5 Hz, CH of $CH_2N$); 3.35 (1H, d, J=4.1 Hz, CH-bridgehead); 8.02 (1H, s, pyrazine-H).

4. exo and endo-3-[2-(3,5-Dimethylpyrazin)yl]3-chloro-1-azabicyclo[2.2.1]heptane The title-chlorides were prepared from the preceding alcohol (3.1 g. 14.0 mmol) using the procedure described for Example 8. The crude product was purified by chromatography through alumina eluting with ethyl acetate. The product was obtained as a mixture of diastereoisomers (1.93 g). A sample of the less polar isomer was obtained as a single 509 diastereoisomer; (Found: $M^+$ =237.1021. $C_{12}H_{16}N_3Cl$ requires $M^+$ =237.1033); δ (360 MHz, $CDCl_3$) 0.88–1.00 (1H, m. CH of $CH_2$); 1.62–1.72 (1H, m. CH of $CH_2$): 2.28–2.36 (1H, m, CH of $CH_2N$); 2.53 (3H. s, Me); 2.67 (1H, dd, J=2.4 and 9.8 Hz, CH of $CH_2N$); 2.74–2.82 (1H, m, CH of $CH_2N$); 2.77 (3H, s, Me); 3.40 (1H d, J=9.8 Hz, CH of $CH_2N$); 3.46 (1H, d, J=4.10 Hz, CH-bridgehead); 3.51 (1H, d, J=13.8 Hz, CH of $CH_2N$); 4.22–4.34 (1H, m, CH of $CH_2N$); 8.19 (1H s, pyrazine-H).

5. endo-3-2-(3,5-Dimethylpyrazin)yl]-1azabicyclo[2.2.1]heptane. Dihydrochloride A mixture of the preceding chlorides (1.83 g, 7.7 mmol) was hydrogenated in the usual way. Chromatography of the crude Product through alumina, eluting with dichloromethane/methanol (99:1) gave the title-endo-pyrazine (1.2 g). The dihydrochloride salt was prepared, m.p. 217°–220° C. (isopropyl alcohol): (Found: C. 48.83; H, 6.99; N, 14.11. $C_{12}H_{17}N_3$. 2 $HCl.H_2O$ requires C, 48.99; H, 7.19; N, 14.28%); δ (360 MHz, $D_2O$) 1.46–1.52 (1H, m, CH of $CH_2$); 1.86–1.96 (1H, m, CH of $CH_2$); 2.68 (3H, s, Me); 2.75 (3H, s, Me); 3.38–3.51 (4H, m, 3 of CH of $CH_2N$, and CH-bridgehead); 3.61 (1H, d, J=9.2 Hz, CH of $CH_2N$); 3.73 (1H, dd J=11.2 and 11.4 Hz, CH of $CH_2N$); 4.00–4.05 (1H, m, CH of $CH_2N$); 4.28–4.34 (1H, m, CH-pyrazine); 8.82 (1H, s, pyrazine-H).

EXAMPLE 52 exo-3-2-(3,5-Dimethylpyrazin)yl]-1-azabicyclo[2.2.1]heptane Dihydrochloride

The less polar product obtained from the chromatography of Example 51 Part 5 was identified as the title -exo-pyrazine (0.1 g). The dihydrochloride salt was prepared, m.p. 205° C. (dec) (isopropyl alcohol/ether): (Found: C, 49.23; H, 6.73; N, 14.27 $C_{12}H_{17}N_3$ 2.1. HCl 0.7 $H_2O$ requires C, 49.28; H, 7.07; N, 14.37%); m/e 203 $M^+$); δ (360 MHz, $D_2O$) 2.02–2.10 (1H. m CH of $CH_2$); 2.20–2.29 (1H, m, CH of CH ); 2.63 (3H, s, Me); 2.70 (3H, s, Me); 3.12 (1H, d, J=4.4 Hz, CH-bridgehead); 3.18 (1H, d, J=9.4 Hz, CH of $CH_2N$); 3.35–3.45 (1H, m CH of $CH_2N$); 3.50–3.60 (2H, m, 2 of CH of $CH_2N$); 3.61–3.67 (1H, m, CH of $CH_2N$); 3.77 (1H, dd, J=5.6 and 8.3 Hz, CH of $CH_2N$); 4.06–4.11 (1H, m, C̄H-pyrazine); 8.67 (1H, s, pyrazine-H).

EXAMPLE 53 exo and endo-3-[2-(6-propargyloxypyrazin)yl]-1azabicyclo[2.2.1]heptane. Hydrochloride Sodium hydride (150 mg of an 80% dispersion in oil. 5.2 mmol) was added to a solution of propargyl alcohol (0.3 g, 5.4 mmol) in anhydrous toluene (20 ml) and heated at 70° C. for 0.1 h. A solution of endo-3-[2-(6-chloropyrazin)yl]-1-azabicyclo[2.2.1]heptane (0.3 g, 1.43 mmol Example 48) in toluene (1 ml) was added to the reaction mixture and heated at 130° C. for 36 h. The solvent was removed under vacuum. The residue taken up into dichloromethane (70 ml) and washed with water (20 ml). The aqueous was extracted with dichloromethane ($3 \times 50$ ml), the combined extracts dried ($Na_2SO_4$), and evaporated, and the residue purified by chromatography through alumina eluting with dichloromethane/methanol (99:1). The more polar product (0.11 g), the endo-diastereoisomer was obtained as a crystalline solid. The hydrochloride salt was prepared. m.p. 213°–215° C. (isopropyl alcohol/ether); (Found: C, 58.48; H. 6.11; N, 15.74. $C_{13}H_{15}N_3O.HCl$ requires C, 58.76; H, 6.08; N, 15.81%); m/e 229 $M^+$); δ (360 MHz, $D_2O$) 1.78–1.98 (2H, m $CH_2$); 2.95 (1H, t, J=2.4 Hz, alkyne-H); 3.30 (1H, br s C̄H-bridgehead); 3.39 (1H, d, J=9.1 Hz, CH of $CH_2N$) 3.50–3.58 (3H, m, 3 of CH of $CH_2N$); 3.75 (1H, dd, J=11.3 and 11.8 Hz, CH of $CH_2N$); 3.89–3.95 (1H, m, CH of $CH_2N$); 4.04–4.10 (1H, m, C̄H-pyrazine); 5.04 (1H, dd, J=2.4 and 15.8 Hz, CH of $CH_2O$); 5.17 (1H, dd, J=2.4 and 15.8 Hz, CH of $CH_2O$); 8.18 (1H, s, pyrazine-H); 8.21 (1H, s, pyrazine-H). The less Polar component was identified as the exo-diastereoisomer (20 mg); m/e 229 ($M^+$).

EXAMPLE 54

3-[2-(6-n-Butyloxypyrazin)yl]-1-azabicyclo[2.2.2]octane. Hydrochloride

Sodium (0.13 g. 5.7 mmol) was added to n-butanol (5 ml) and heated at 80° C. for 0.5 h. A solution of 3-[2-(6-chloropyrazin)yl]-1-azabicyclo[2.2.2]octane (0.25 g. 1.17 mmol. Example 46). in butanol (5 ml) was added and the reaction mixture heated at reflux for 16 h. The solvent was removed under vacuum. The residue taken up into dichloromethane (50 ml) and washed with water (20 ml). Drying ($Na_2SO_4$) and evaporation were followed by chromatography through alumina eluting with dichloromethane/methanol (98:2) to give the title -butyloxypyrazine (80 mg). The hydrochloride salt was prepared, m.p. 148°–149° C.; (Found: C, 57.21; H, 7.61; N, 13.11. $C_{15}H_{23}N_3O$. 1.5 HCl requires C, 57.01; H, 7.76; N, 13.30%): m/e 261 ($M^+$): δ (360 MHz, $D_2O$) 0.95 (3H, t, J=7.4 Hz. Me); 1.41–1.52 (2H, m, $CH_2$); 1.75–1.82 (3H, m, $CH_2$ and CH of $CH_2$); 1.88–2.02 (1H m, CH of $CH_2$); 2.10–2.24 (2H, m, $CH_2$); 2.34–2.37 (1H, m, CH-bridgehead); 3.33–3.72 (6H, m, 3 of $CH_2N$); 3.99 (1H, dd, J=5 and 12.1 Hz, CH-pyrazine): 4.42–4.47

(2H, m, CH$_2$O); 8.08 (1H, s, pyrazine-H); 8.12 (1H, s, pyrazine-H).

EXAMPLE 55 endo-3-[2-(3.5.6-trimethylpyrazin)yl]-1-azabicyclo[2.2.1]heptane. Hydrochloride

1. 2-Hydroxy-3,5,6-trimethylpyrazine

The title-hydroxypyrazine was prepared from alanine amide hydrochloride and 2,3-butanedione as described by Karmas and Spoerri, *J. Am. Chem. Soc.*, 1952, 74, 1580, δ (60 MHz, CDCl$_3$) 2.25 (6H, s, 2 of Me); 2.40 (3H, s, Me).

2. 2-Iodo-3,5,6-trimethylpyrazine

This was prepared from the chloride using the iodination procedure described by Hirschberg and Spoerri, *J. Org. Chem.*, 1961 1907. m.p. 59.0°–63.0° C.; δ (360 MHz, CDCl$_3$) 2.44 (3H, s, Me); 2.47 (3H, s, Me); 2.69 (3H, s, Me).

3. exo-3-[2-(3,5,6-Trimethylpyrazin)yl]-1azabicyclo[2.2.1]heptan-3-ol

The title-compound was prepared from 1-azabicyclo[2.2.1]heptan-3-one (2.1 g. 18.9 mmol) and 2-iodo-3,5,6-trimethylpyrazine (4.7 g. 18.9 mmol) using the procedure described for Example 1. The crude product was purified by alumina chromatography eluting with dichloromethane/methanol (97:3). The product (1.64 g) was obtained as a crystalline solid. m.p. 200°–204° C.; (Found: M$^+$=233.1523. C$_{13}$H$_{19}$N$_3$ O requires M$^-$=233.15281); & (360 MHz, CDCl$_3$) 1.48–1.57 (1H, m, CH of CH$_2$); 2.14–2.24 (1H m CH of CH$_2$); 2.34 (1H, dd, J=3.5 and 9.8 Hz, CH of CH$_2$N); 2.40 (3H, s, Me); 2.45 (SH, s, Me); 2.45–2.50 (1H, m, CH of CH$_2$N); 2.55 (3H, s, Me); 2.57 (1H, dd, J=3.6 and 12.6 Hz, CH of CH$_2$N); 2.62–2.72 (1H, m, CH of CH$_2$N); 2.80–2.88 (1H, m, CH of CH$_2$N); 3.26 (1H, dd, J=1.9 and 12.6 Hz, CH of CH$_2$N); 3.42 (1H, d, J=4.1 Hz, CH-bridgehead).

4. 3-[2-(3,5,6-Trimethylpyrazin)yl]-1-azabicyclo]2.2.1-]hept-2-ene and endo-3-[2-(3,5,6-trimethyl pyrazin)yl]-3-chloro-1-azabicyclo[2.2.1]heptane The chloride was prepared from the preceding alcohol (1.6 g. 6.87 mmol) using the procedure described for Example 8. The crude product was Purified by chromatography through silica-gel eluting with dichloromethane/methanol (90:10). The less polar product (0.78 g), identified as the title-chloride. was obtained as a Pale red oil. (Found: M$^+$=251.1176. C$_{13}$H$_{18}$N$_3$Cl requires M$^+$=351.11893); δ (250 MHz, CDCl$_3$) 1.62–1.86 (2H, m, CH$_2$); 2.36–2.46 (1H, m, CH of CH$_2$N); 2.48 (3H, s, Me): 2.50 (3H, s, Me); 2.50–2.58 (1H, m, CH of CH$_2$N); 2.62 (3H, s, Me); 2.76–2.84 (1H, m, CH of CH$_2$N); 2.96–3.04 (1H, m, CH of CH$_2$N); 3.10 (1H, dd, J=3.5 and 13.2 Hz, CH of CH$_2$N); 3.84 (1H, dd, J=2 and 13.2 Hz, CH of CH$_2$N); 3.92 (1H, d, J=4.2 Hz, C$\underline{H}$-bridgehead).

The more polar product was identified as the elimination product (0.1 g): (Found: M$^+$=215.1404. C$_{13}$H$_{17}$N$_3$ requires M$^+$=215.14225); δ (250 MHz, D$_2$O, hydrochloride salt) 1.80–1.94 (1H, m, CH of CH$_2$); 2.42–2.58 (1H, m, CH of CH$_2$); 2.63 (9H, s, 3 of Me); 3.28 (1H, d, J=8 Hz, CH of CH$_2$N); 3.26–3.38 (1H, m, CH of CH$_2$N); 3.50–3.55 (1H, m, CH of CH$_2$N); 3.88–3.98 (1H, m, CH of CH$_2$N); 4.27 (1H, d, J=4 Hz, CH-bridgehead); 7.17 (1H, s, vinyl-H).

5. endo-3-[2-(3,5,6-Trimethylpyrazin)yl]-1azabicyclo[2.2.1]heptane. Hydrochloride The preceding chloride (0.7 g. 3.0 mmol) was hydrogenated in the usual way. The crude product was chromatographed through silica-gel eluting with dichloromethane/methanol/concn. ammonia (89:10:1) to give the endo-diastereoisomer (0.57 g). The hydrochloride salt was prepared, m.p. 222° C. (dec) (isopropyl alcohol/ether); (Found: M$^+$=217.1585. C$_{13}$H$_{19}$N$_3$ requires M$^+$=217.15790); δ (360 MHz. D$_2$O) 1.44–1.54 (1H, m, CH of CH$_2$); 1.83–1.94 (1H, m, CH of CH ); 2.67 (3H, s, Me); 2.68 (3H, s, Me); 2.70 (3H, s, Me); 3.34–3.39 (1H, m, CH-bridgehead); 3.41 (1H, dd, J=2 and 9.1 Hz, CH of CH$_2$N); 3.46–3.54 (2H m, 2 of CH of CH$_2$N); 3.59 (1H, d, J=9.1 Hz, CH of CH$_2$N); 3.65–3.72 (1H, m, CH of CH$_2$N); 4.05–4.12 (1H, m, CH of CH$_2$N); 4.22–4.30 (1H, m, C$\underline{H}$-pyrazine).

EXAMPLE 56 exo-3-2-(3,5,6-trimethylpyrazin)yl]-1-azabicyclo[2.2.1]heptane. Dihydrochloride

The less polar product obtained from the chromatography of Example 55 part 5 was identified as the title-exo-diastereoisomer (36 mg). The dihydrochloride salt was prepared. m.p. 180° C. (dec) (isopropyl alcohol/ether); (Found: C, 51.85; H, 7.45; N, 13.74.C$_{13}$H$_{17}$N$_3$2 HCl.0.6 H$_2$O requires C, 51.87; H. 7.43; N, 13.93%); δ (360 MHz, D$_2$O) 2.01–2.10 (1H, m, CH of CH$_2$); 2.20–2.28 (1H, m, CH of CH$_2$); 2.65 (6H, s, 2 of Me); 2.70 (3H, s Me); 3.08 (1H, d, J=4.3 Hz, CH-bridgehead); 3.16 (1H, d, J=9.3 Hz, CH of CH$_2$N); 3.34–3.42 (1H, m, CH of CH$_2$N); 3.48–3.67 (3H, m, 3 of CH of CH$_2$N); 3.74–3.78 (1H, m, CH of CH$_2$N); 4.14–4.20 (1H, m, CH-pyrazine).

EXAMPLE 57 exo and endo-3-[2-(5,6-Dimethylpyrazin)yl]-1azabicyclo[2.2.1]heptane. Hydrogen Oxalate

1. 2-Hydroxy-5,6-dimethylpyrazine

The title-hydroxypyrazine was prepared from glycine amide hydrochloride and 2.3-butanedione as described by Karmas and Spoerri. *J. Am. Chem. Soc.*, 1952, 74, 1580, m.p. 197°–198° C. (Lit. 201°–202° C.).

2. 2-Iodo-5,6-dimethylpyrazine

The preceding hydroxypyrazine was converted to the chloride using the procedure of Karmas et al and this then converted to the title-iodide using the procedure of Hirschberg and Spoerri, *J. Org. Chem.*, 1961, 1907, m.p. 51°–54° C. (Lit. 55°–57° C.).

3. exo-3-[2-(5,6-Dimethylpyrazin)yl-1-azabicyclo[2.2.1]heptan-3-ol

The title-alcohol was prepared from 1-azabicyclo[2.2.1]heptan-3-one (3 g. 27.0 mmol) and 2-iodo-5,6-dimethylpyrazine (6.32 g. 27.0 mmol) using the general halogen/metal exchange procedure. Chromatography through alumina eluting with dichloromethane/methanol (97:3) gave the Pure product (2.67 g). m.p. 153°–157° C. (Found: M$^+$=219.1374.C$_{12}$H$_{17}$N$_3$O requires M+ =219.1372); δ (360 MHz, CDCl₃) 1.48-1.57 (1H, m, CH of CH₂); 2.00 (1H, br s, OH); 2.33-2.46 (1H, m, CH of CH₂); 2.47 (1H, dd, J=4 and 10.1 Hz, CH of CH₂N); 2.53 (3H, s, Me); 2.54 (3H, s, Me); 2.60 (1H, dd, J=3.7 and 12.9 Hz CH of CH₂N); 2.65 (1H, d, J=4 Hz, CH-bridgehead); 2.76-2.84 (1H, m, CH of CH₂N); 2.93-3.03 (2H, m, 2 of CH of CH₂N); 3.35 (1H, dd, J=2.0 and 12.9 Hz, CH of CH₂N) 8.48 (1H, s, pyrazine-H).

4. 3-[2-(5,6-Dimethylpyrazin)yl]-3-chloro-1azabicyclo[2.2.1]heptane

This was prepared from the Preceding alcohol (2 g, 9.13 mmol) using the general procedure. The crude product was purified by alumina chromatography eluting with ethyl acetate. The product (0.52 g) was obtained as a crystalline solid, m.p. 88°-89° C.; (Found: M+ =237.1039.C₁₁H₁₆N₃Cl requires M+ =237.1033); δ (360 MHz, CDCl₃) 0.91-0.98 (1H, m, CH of CH ); 1.55-1.64 (1H, m, CH of CH₂); 2.36-2.46 (1H, m CH of CH₂N); 2.53 (3H, s, Me); 2.54 (3H, s, Me); 2.66 (1H, dd J=2.8 and 10 Hz, CH of CH₂N); 2.74-2.83 (1H, m CH of CH₂N); 3.21 (1H, d, J=4.5 Hz, CH-bridgehead); 3.40 (1H, d, J=10 Hz, CH of CH₂N); 3.45 (1H, dd, J=2.1 and 13.8 Hz, CH of CH₂N); 4.09 (1H, dd, J=2.8 and 13.8 Hz, CH of CH₂N); 8.56 (1H, s, pyrazine-H).

5. exo- and endo-3-[2-(5.6-Dimethylpyrazin)yl]-1-azabicyclo[2.2.1-]heptane. Hydrogen Oxalate Hydrogenation of the preceding chloride (0.52 g. 2.20 mmol) using the general procedure gave a mixture of the title-diastereoisomers which were separated by chromatography through alumina eluting with dichloromethane/methanol (99.5:0.5). The less polar product (60 mg) was identified as the exo-isomer. The hydrogen oxalate salt was prepared, m.p. 143°-144° C. isopropylalcohol/ether); (Found: M+ =203.1406.C₁₂H₁₇N₃ requires M+ =203.14225); (δ 360 MHz. D₂O) 1.94-2.04 (1H, m, CH of CH₂); 2.16-2.28 (1H, m, CH of CH₂); 2.51 (3H, s, Me); 2.54 (3H, s, Me): 3.16 (1H, s, CH-bridgehead): 3.17 (1H, d, J=8.3 Hz, CH of CH₂N): 3.32-3.40 (1H, m, CH of CH₂N); 3.46-3.56 (2H, m, 2 of CH of CH₂N); 3.61-3.68 (2H, m, 2 of CH of CH₂N); 3.87-3.92 (1H, m, CH-pyrazine); 8.27 (1H, s, pyrazine-H).

The more polar product (0.34 g) was identified as the endo-isomer. The hydrogen oxalate salt was prepared, m.p. 165°-168° C. (isopropylalcohol); (Found: M+ =203.1434.C₁₂H₁₇N₃ requires M+ =203.14225); (δ 360 HMz, D₂O) 1.56-1.66 (1H, m, CH of CH₂); 1.88-2.00 (1H, m, CH of CH₂); 2.54 (3H, s, Me): 2.57 (3H, s, Me); 3.33-3.40 (3H, m, 2 of CH of CH₂N and CH-bridgehead); 3.41-3.50 (1H, m CH of CH₂N); 3.55 (1H, d, J=9.2 Hz, CH of CH₂N); 3.79-3.86 (2H, m, 2 of CH of CH₂N); 3.98-4.06 (1H, m, CH-pyrazine): 8.28 (1H s, pyrazine-H).

EXAMPLE 58

6-(2-Pyrazinyl)-2-azabicyclo[2.2.2]octane-Isomers A and B. Hydrochloride

A solution of 6-[2-(6-chloropyrazin)yl]-2-azabicyclo[2.2.2]octane, isomer A (0.2 g, 1.0 mmol, Example 49) in methanol (25 ml) was hydrogenated over Pd/C (50 mg. 10%) for 0.75 h. The catalyst was removed by filtration through hyflo and the solvent removed under vacuum to give 6-(2-pyrazinyl)-2-azabicyclo[2.2.2]octane hydrochloride Isomer A. m.p. 188°-190° C. (methanol/ether); (Found: M+ =189.1283. C₁₁H₁₅N₃ requires M+ =189.1266); δ (360 MHz. D₂O) 1.81-1.90 (3H, m, 3 of CH of CH₂); 2.02-2.18 (3H, m, CH-bridgehead and 2 of CH of CH₂); 2.34-2.43,(1H, m, CH of CH₂); 3.29-3.34 (1H, m, CH of CH₂N); 3.44-3.59 (2H, m, CH of CH₂N and CH-pyrazine); 3.78-3.80 (1H, m, CH-bridgehead); 8.54-8.58 (2H, m, 2 of pyrazine-H); 8.60-8.62 (1H, m, pyrazine-H).

In a similar manner, 6-[2-(6-chloropyrazin)yl]-2azabicyclo[2.2.2]octane, isomer B was converted to 6-(2-pyrazinyl)-2-azabicyclo[2.2.2]octane, isomer B.

EXAMPLE 59

Tablet preparation

Tablets containing 1.0, 2.0. 25.0. 26.0. 50.0 and 100.0 mg, respectively of the following compounds are prepared as illustrated below:

3-(2-pyrazinyl)-1-azabicyclo[2.2.1]heptane, isomers A and B;

3-[2-(6-methoxypyrazin)yl]-1-azabicyclo[2.2.1]heptane, isomers A and B.

| | Amount-mg | | |
|---|---|---|---|
| TABLE FOR DOSES CONTAINING FROM 1-25 MG OF THE ACTIVE COMPOUND | | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |
| TABLE FOR DOSES CONTAINING FROM 26-100 MG OF THE ACTIVE COMPOUND | | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg. 26.0 mg. 50.0 mg, and 100.0 mg of active ingredient per tablet.

What is claimed is:

1. A pyrazine, pyridazine or pyrimidine compound of formula I:

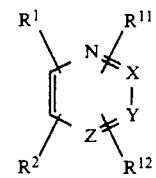

wherein, one of X, Y and Z represents nitrogen and the remainder represent carbon atoms; substituted on one of the ring carbon atoms with a $R^1$ substituent represented by a non-aromatic azacyclic or azabicyclic ring system and independently substituted on each of the other ring carbon atoms with a $R^2$, $R^{11}$ or $R^{12}$ substituent of low lipophilicity or a hydrocarbon having a maximum of 20 carbon atoms, salt or prodrug thereof.

2. The compound according to claim 1, wherein $R^2$, $R^{11}$ and $R^{12}$ are independently selected from the group consisting of hydrogen, halogen, $-CF_3$, $-OR^6$, $-NR^6R^7$, $-NHOR^6$, $-NHNH_2$, $-CN$, $COR^8$ and hydrocarbon group which is unsubstituted or substituted with an halogen, $-OR^6$, $CF_3$, $-NR^6R^7$, $-NO_2$, aryl optionally substituted with a substituent selected from the group consisting of chloro, bromo, methoxy, $C_{1-6}$ alkyl, methoxycarbonyl, trifluoromethyl, nitro and $-NR^6R^7$ substituent; wherein $R^6$ is selected from the group consisting of hydrogen, $C_{1-6}$ alkyl, $C_{2-6}$ alkenyl and $C_{2-6}$ alkynyl; $R^7$ is selected from the group consisting of hydrogen, $C_{1-6}$ alkyl and $-COCH_3$; and $R^8$ represents $-OR^6$ or $-NR^6R^7$.

3. The compound according to claim 1 represented by formula IIA, IIB or IIC:

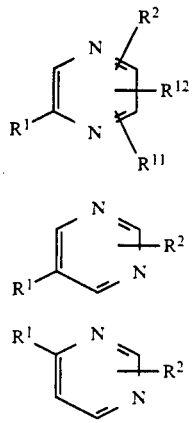

wherein $R^1$, $R^2$, $R^{11}$ and $R^{12}$ are independently selected from the group consisting of hydrogen, halogen, $-CF_3$, $-OR^6$, $-NR^6R^7$, $-NHOR^6$, $-NHNH_2$, $-CN$, $COR^8$ and hydrocarbon group which is unsubstituted or substituted with an halogen, $-OR^6$, $CF_3$, $-NR^6R^7$, $-NO_2$, aryl optionally substituted with a substituent selected from the group consisting of chloro, bromo, methoxy, $C_{1-6}$ alkyl, methoxycarbonyl, trifluoromethyl, nitro and $-NR^6R^7$ substituent; wherein $R^6$ is selected from the group consisting of hydrogen, $C_{1-6}$ alkyl, $C_{2-6}$ alkenyl and $C_{2-6}$ alkynyl; $R^7$ is selected from the group consisting of hydrogen, $C_{1-6}$ alkyl and $-COCH_3$; and $R^8$ represents $-OR^6$ or $-NR^6R^7$.

4. The compound according to claim 1, wherein the non-aromatic azacyclic or azabicyclic ring system is selected from the group consisting of pyrrolidine, quinuclidine, tetrahydropyridine, piperidine, dehydrotropane, pyrrolizidine, azanorbornane, isoquinuclidine and azabicyclo[2.2.2]octene, any of said groups may be optionally substituted with a substituent selected from the group consisting of $C_{1-3}$ alkyl, hydroxy, halogen and $C_{1-3}$ alkoxycarbonyl.

5. The compound according to claim 2, wherein $R^2$, $R^{11}$ and $R^{12}$ are independently selected from the group consisting of hydrogen, halogen, $-OR^6$, $C_{1-6}$ alkyl, phenyl($C_{1-3}$)alkyl, $C_{3-6}$ cycloalkyl, amino and dimethylamino, in which $R^6$ is as defined in claim 2.

6. The compound according to claim 1 selected from the group consisting of:
3-(2-pyrazinyl)-1-azabicyclo[2.2.2]octan-3-ol;
3-(2-pyrazinyl)-1-azabicyclo[2.2.2]octane;
3-[2-(6-methylpyrazin)yl]-1-azabicyclo[2.2.2]octan-3-ol;
3-[2-(6-methylpyrazin)yl]-1-azabicyclo[2.2.2]octane;
3-[2-(6-methoxypyrazin)yl]-1-azabicyclo[2.2.2]octane;
3-[2-(6-hydroxypyrazin)yl]-1-azabicyclo[2.2.2]-octane;
3-(2-pyrazinyl)-1-azabicyclo[2.2.1]heptan-3-ol;
3-(2-pyrazinyl)-1-azabicyclo[2.2.1]heptane;
6-(2-pyrazinyl)-1-azabicyclo[3.2.1]octan-6-ol;
6-(2-pyrazinyl)-1-azabicyclo[3.2.1]octane;
3-(5-pyrimidinyl)-1-azabicyclo[2.2.2]octan-3-ol;
3-(5-pyrimidinyl)-1-azabicyclo[2.2.2]octane;
3-[5-(2-methylpyrimidin)yl]-1-azabicyclo[2.2.2]octane;
3-(2-pyrazinyl)-1-azabicyclo[2.2.1]heptan-5-ol;
3-fluoro-3-(2-pyrazinyl)-1-azabicyclo[2.2.1]heptane;
1-methyl-3-(2-pyrazinyl)pyrrolidine;
3-[2-(6-methoxypyrazin)yl]-1-azabicyclo[2.2.1]heptane;
3-[2-(3-methylpyrazin)yl]-1-azabicyclo[2.2.2]octan-3-ol;
3-[2-(3-methylpyrazin)yl]-3-chloro-1-azabicyclo[2.2.2]octane;
3-[2-(3-methylpyrazin)yl]-1-azabicyclo[2.2.2]oct-2-ene;
3-[2-(3-methylpyrazin)yl]-1-azabicyclo[2.2.2]octane;
3-[2-(6-methylpyrazin)yl]-1-azabicyclo[2.2.1]heptan-3-ol;
3-[2-(6-methylpyrazin)yl]-3-chloro-1-azabicyclo[2.2.1]heptane;
3-[2-(6-.methylpyrazin)yl]-1-azabicyclo[2.2.1]heptane;
3-[2-(6-dimethylaminopyrazin)yl]-1-azabicyclo[2.2.1]heptan-3-ol;
3-[2-(6-dimethylaminopyrazin)yl]-1-azabicyclo[2.2.1]heptane;
3-[2-(6-ethoxypyrazin)yl]-1-azabicyclo[2.2.1]heptan-3-ol;
3-[2-(6-ethoxypyrazin)yl]-1-azabicyclo[2.2.1]heptane;
6-[2-(6-methoxypyrazin)yl]-1-azabicyclo[3.2.1]octane;
3-[2-(3,6-dimethylpyrazin)yl]-1-azabicyclo[2.2.1]-heptan-3-ol;
3-[2-(3,6-dimethylpyrazin)yl]-1-azabicyclo[2.2.1]heptane;
3-[2-(3,5-dimethylpyrazin)yl]-1-azabicyclo[2.2.1]heptane;
3-[5-(2,3-dimethylpyrazin)yl]-1-azabicyclo[2.2.1]heptane;
3-[2-(3-ethylpyrazin)yl]-1-azabicyclo[2.2.2]octane;
3-[2-(3-ethylpyrazin)yl]-1-azabicyclo[2.2.1]heptane;
3-[2-(6-isopropoxypyrazin)yl]-1-azabicyclo[2.2.1]heptane;
3-[2-(6-propargyloxypyrazin)yl]-1-azabicyclo[2.2.1]heptane;
3-[2-(6-chloropyrazin)yl]-3-methoxycarbonyl-1-azabicyclo[2.2.2]octane;
3-[2-(6-chloropyrazin)yl]-1-azabicyclo[2.2.2]octane;
3-[2-(5-methylpyrazin)yl]-1-azabicyclo[2.2.2]octane;
3-[2-(6-allyloxypyrazin)yl]-1-azabicyclo[2.2.2]octane;
3-[2-(3-methylpyrazin)yl]-1,2,5,6-tetrahydropyridine;
3-[2-(6-methylpyrazin)yl]-1,2,5,6-tetrahydropyridine;
6-[2-(6-methylpyrazin)yl]-2-azabicyclo[2.2.2]octane;
6-[2-(3-methylpyrazin)yl]-2-azabicyclo[2.2.2]octane;
3-[2-(6-allyloxypyrazin)yl]-1-azabicyclo[2.2.1]heptane;
3-[2-(3-methylpyrazin)yl]-1-azabicyclo[2.2.1]heptane;
3-[2-(6-chloropyrazin)yl]-1-azabicyclo[2.2.1]heptane;
6-[2-(6-chloropyrazin)yl]-2-azabicyclo[2.2.2]octane;
6-[2-(6-methoxypyrazin)yl]-2-azabicyclo[2.2.2]octane;
3-[2-(6-n-butoxypyrazin)yl]-1-azabicyclo[2.2.2]octane;
3-[2-(3,5,6-trimethylpyrazin)yl]-1-azabicyclo[2.2.1]heptane;
6-(2-pyrazinyl)-2-azabicyclo[2.2.2]octane; and
3-[4-(2-chloropyrimidin)yl]-1-azabicyclo[2.2.1]heptane.

7. A pharmaceutical composition comprising an effective amount of a compound according to claim 1 in association with a pharmaceutically acceptable carrier.

8. The composition according to claim 7 further comprising a peripheral cholinergic antagonist.

9. A method for the treatment of neurological and mental disorders which comprises administering to a patient in need of such treatment an effective amount of a compound according to claim 1.

* * * * *